(12) United States Patent
Lee et al.

(10) Patent No.: US 10,596,522 B2
(45) Date of Patent: Mar. 24, 2020

(54) HEMOLYSIS-FREE BLOOD PLASMA SEPARATION

(71) Applicant: THE REGENTS OF THE UNIVERSITY OF CALIFORNIA, Oakland, CA (US)

(72) Inventors: Luke P. Lee, Orinda, CA (US); Jun Ho Son, Richmond, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 171 days.

(21) Appl. No.: 15/567,919

(22) PCT Filed: Apr. 25, 2016

(86) PCT No.: PCT/US2016/029143
§ 371 (c)(1),
(2) Date: Oct. 19, 2017

(87) PCT Pub. No.: WO2016/172675
PCT Pub. Date: Oct. 27, 2016

(65) Prior Publication Data
US 2018/0200677 A1  Jul. 19, 2018

Related U.S. Application Data

(60) Provisional application No. 62/152,246, filed on Apr. 24, 2015.

(51) Int. Cl.
*B01L 99/00*   (2010.01)
*B01D 63/08*   (2006.01)
*B01L 3/00*    (2006.01)
*A61B 5/15*    (2006.01)

(52) U.S. Cl.
CPC ...... *B01D 63/088* (2013.01); *A61B 5/150022* (2013.01); *A61B 5/150358* (2013.01); *B01L 3/502753* (2013.01); *B01L 2300/0681* (2013.01); *B01L 2300/087* (2013.01); *B01L 2300/0816* (2013.01); *B01L 2300/0874* (2013.01); *B01L 2300/0883* (2013.01); *B01L 2300/0887* (2013.01); *B01L 2400/049* (2013.01)

(58) Field of Classification Search
None
See application file for complete search history.

(56) References Cited

U.S. PATENT DOCUMENTS

| 2004/0053422 | A1  | 3/2004 | Chan et al. |
| 2009/0120865 | A1* | 5/2009 | Chung ............ B01L 3/502753 |
|              |     |        | 210/232 |
| 2010/0112723 | A1* | 5/2010 | Battrell ................ G01N 33/53 |
|              |     |        | 436/501 |

FOREIGN PATENT DOCUMENTS

WO   WO 2016/172675 A1   10/2016

OTHER PUBLICATIONS

Al-Soud, et al., *J. Clin. Microbiol.*, 2001, 39(2):485-493.
(Continued)

*Primary Examiner* — Paul S Hyun
(74) *Attorney, Agent, or Firm* — Morgan, Lewis & Bockius LLP; Jeffry S. Mann; Todd Esker

(57) ABSTRACT

A simple and robust on-chip blood plasma separation device is provided. The device is configured to integrate with downstream detection modules and provides sample-to-answer microfluidic POC diagnostics devices.

21 Claims, 19 Drawing Sheets

(56) References Cited

OTHER PUBLICATIONS

Cheng, et al., *Chest*, 2005, 128:1453-1460.
Chin, et al., *Lab Chip*, 2007, 7:41-57.
Chin, et al., *Nat. Medicine*, 2011, 17:1015-1019.
Chin, et al., *Lab Chip*, 2012, 12:2118-2134.
Cho, et al., *Lab Chip*, 2007, 7:565-573.
Davis, et al., *Proc. Natl. Acad. Sci. U. S. A.*, 2006, 103:14779-14784.
Dimov, et al., *Lab Chip*, 2011, 11:845-850.
Ji, et al., *Biomed Microdevices*, 2008, 10:251-257.
Kabanova, et al., *Int. J. Med. Sci.* 2009, 6(4):156-159.
Kersaudy-Kerhoas, et al., *Lab Chip*, 2013, 13:3323-3346.
Kirschner, et al., *PLoS One*, 2011, 6(9):e24145.
Lee, et al., *Lab Chip*, 2013, 13:3261-3267.
Lenshof, et al., *Anal. Chem.*, 2009, 81:6030-6037.
Lippi, et al., *Critical Reviews in Clinical Laboratory Sciences*, 2011, 48(3):143-153.
Mach, et al., *Biotechnol. Bioeng.*, 2010, 107:302-311.
Phillips, et al., *Physical Review Lett.*, 2012, 109:118105.
Randall, et al., *Proc. Natl. Acad. Sci. U. S. A.*, 2005, 102:10813-10818.
Shardt, et al., *International Journal of Multiphase Flow*, 2012, 47:25-36.
Son et al., *Lab Chip*, 2014, 14 (13): 2287-2292.
Song, et al., *Nat. Communication*, 2012, 3:1283.
Sozzi, et al., *J. Clin. Oncol.* 2003, 21:3902-3908.
Thorslund, et al., *Biomed Microdevices*, 2006, 8:73-79.
Wang et al., *Nanomedicine*, 2012, 7: 5019-5028.
Wei et al., *Lab Chip*, 2011, 11(2): 238-245.
Yager, et al., *Nature*, 2006, 442:412-418.
Zhang, et al., *Anal. Chem.*, 2012, 84:3780-3786.

\* cited by examiner

FIG. 5A
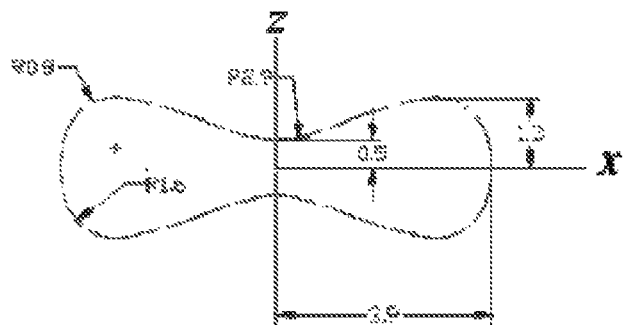
FIG. 5B
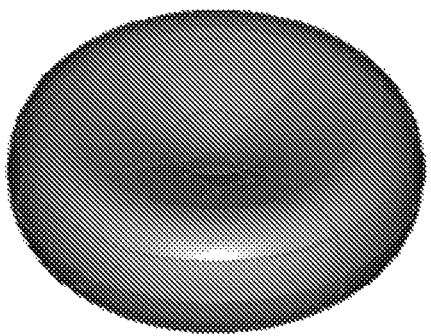
FIG. 5C
| Direction | x | y | x |
|---|---|---|---|
| Drag force coefficient [N·sec/m] | $1.32 \times 10^{-7}$ | $1.32 \times 10^{-7}$ | $2.03 \times 10^{-7}$ |

HEMOLYSIS-FREE BLOOD PLASMA SEPARATION

CROSS REFERENCE TO RELATED APPLICATIONS

This application claims the benefit under 35 U.S.C. § 119(e) of U.S. Provisional Application No. 62/152,246 filed on Apr. 24, 2015, which is incorporated herein by reference in its entirety for all purposes.

BACKGROUND OF THE INVENTION

Introduction

Blood plasma is the liquid phase of whole blood, containing a large number of biomarkers including proteins, nucleic acids and other metabolites (Kersaudy-Kerhoas, et al., *Lab Chip,* 2013, 13:3323-3346). Due to cellular components (such as red blood cells, white blood cells and platelets) in whole blood that inhibit sensitive, accurate and reproducible diagnostic capabilities, the separation of blood plasma becomes a critical step for most blood-based diagnostic procedures. Although centrifugation is the traditional bench top method for blood plasma separation, it is a time consuming and labor intensive method. Furthermore, centrifugation under improper conditions can lead to hemolysis of red blood cells (RBCs) (Lippi, et al., *Critical Reviews in Clinical Laboratory Sciences,* 2011, 48(3):143-153), resulting in possible plasma contamination. Inhibitors released from the RBCs can hinder effective subsequent protein analysis using immunoassay techniques (L. J. Kricka, *Clinical Chemistry,* 2000, 46(8):1037-1038) and nucleic acid analysis using polymerase chain reaction (PCR) (Al-Soud, et al., *J. Clin. Microbiol.,* 2001, 39(2):485-493). Elevation of microRNA levels in plasma due to hemolysis can also deteriorate the accurate detection of microRNA (Kirschner, et al., *PLoS ONE,* 2011, 6(9):e24145). Also, there is evidence that RBCs can release low levels of messenger RNA in hemolysis (Kabanova, et al., *Int. J. Med. Sci.* 2009, 6(4):156-159).

Recently, microfluidic lab-on-a-chip (LOC) devices for point-of-care (POC) diagnostics have been widely investigated for the rapid detection of infectious diseases (Chin, et al., *Nat. Medicine,* 2011, 17:1015-1019; Song, et al., *Nat. Communication,* 2012, 3:1283; Yager, et al., *Nature,* 2006, 442:412-418). Automation and integration of a blood plasma separation step in the LOC device is ideal for POC diagnostics (Chin, et al., *Lab Chip,* 2007, 7:41-57; Chin, et al., *Lab Chip,* 2012, 12:2118-2134). Numerous microfluidic-based techniques for whole blood separation have been proposed, including geometrical obstacles (Davis, et al., *Proc. Natl. Acad. Sci. U.S.A.,* 2006, 103:14779-14784), sedimentation (Zhang, et al., *Anal. Chem.,* 2012, 84:3780-3786; Dimov, et al., *Lab Chip,* 2011, 11:845-850), acoustic forces (Lenshof, et al., *Anal. Chem.,* 2009, 81:6030-6037), inertial force (Mach, et al., *Biotechnol. Bioeng.,* 2010, 107:302-311), CD type centrifugation (Cho, et al., *Lab Chip,* 2007, 7:565-573), and micro-filtration (Lee, et al., *Lab Chip,* 2013, 13:3261-3267; Ji, et al., *Biomed Microdevices,* 2008, 10:251-257; Thorslund, et al., *Biomed Microdevices,* 2006, 8:73-79). However, most of these techniques have limitations such as complex fabrication processes, dilution of whole blood, and external pump or setup for fluid actuation and operation, making these techniques unsuitable for POC application. Among these techniques, a membrane filter-based blood plasma separation allows for a simple solution to on-chip blood plasma separation, with low fabrication cost and easy integration (Thorslund, et al., *Biomed Microdevices,* 2006, 8:73-79). However, RBC leakage as well as hemolysis of RBCs with high hematocrit level due to clogging at the filter, are severe drawbacks of previously developed membrane filter-based separation methods. Therefore, the need for a simple and reliable on-chip blood plasma separator with high purity plasma and autonomous fluid actuation for POC diagnostics devices still remains.

A device and method for obtaining hemolysis-free blood plasma separation, e.g., for POC diagnostics, would represent a significant advance in the art and would provide a solution to the problems set forth above.

BRIEF SUMMARY OF THE INVENTION

The present invention solves many of the problems with conventional devices and methods for separating nucleic acids from other celluar components of cells such as red blood cells (RBCs), white blood cells, and platelets). In exemplary embodiments, the present invention provides a microfluidic device for separating celluar components from plasma, which is configured to minimize hemolysis of RBCs during the separation. The membrane filter for cellular components filtration is placed on top of a vertical up-flow channel (filter-in-top design) to reduce clogging of cells by gravity-assisted cellular sedimentation. This device demonstrates high on-chip protein and nucleic acid recovery. This simple and reliable blood plasma separation platform can be easily integrated with downstream detection module in lab-on-a-chip (LOC) devices for point of care (POC) diagnostics.

In an exemplary embodiment, the invention provides a microfluidic device for separating nucleic acids (e.g., DNA) from cells (e.g., red blood cells). An exemplary device includes a substrate incorporating a cathode cell and an anode cell. Downstream from the cathode cell and in fluidic communication therewith, is a sample cell into which a sample (e.g., blood) is supplied. Further downstream of the cathode cell, and in fluidic communication with the sample cell is a collection cell into which the nucleic acid migrates and is collected. Downstream from the collection cell and in fluidic communication therewith is the anode. In an exemplary embodiment, H+ is generated at the cathode, and $Cl_2$ is generated at the anode. The cathode, sample cell, collection cell and anode are optionally in communication with each other through one or more gel compartments located therebetween. The gel is permeable to at least one component Also provided are methods of separating plasma and cellular components using a device of the invention. In various embodiments, the method of the invention provides an increase in volume of separated plasma, and a decrease in the hemolysis of RBCs. In an exemplary embodiment, hemolysis is so minimal as to be undetectable. Separated plasma volume was subsequently increased and hemolysis of RBCs was not observed after plasma separation.

The hemolysis-free microfluidic blood plasma separation with a filter-in-top configuration device, and method of using this device can be used in resource-limited settings, such as POC clinical diagnostics in developing countries as well as developed countries, as it has been shown to perform on par with conventional bench-top centrifugation blood plasma separation methods.

Other objects, advantages and embodiments of the invention are apparent from the detailed description that follows.

BRIEF DESCRIPTION OF THE DRAWINGS

FIG. 1. Hemolysis-free blood plasma separation.

FIG. 2. Characterization of blood plasma separation.

FIG. 4. On-chip protein and nucleic acids recovery.

FIG. 5A. dimension of RBCs used for calculation of drag coefficient.

FIG. 5B. Three-dimensional schematic illustration of RBC's

FIG. 5C. Calculated drag coefficient along x-, y- and z-directions.

DETAILED DESCRIPTION OF THE INVENTION

Introduction

Figure 1A:
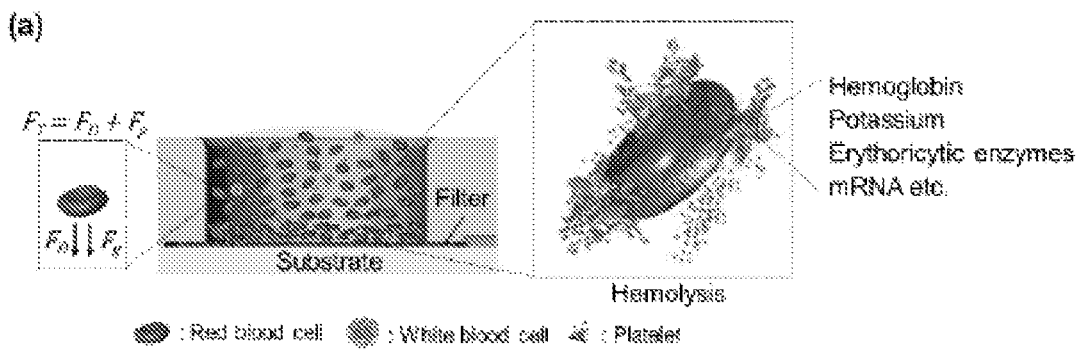
FIG. 1A. Schematic illustration of blood plasma separation with membrane filter. For the filter-in-bottom configuration, RBCs are hemolyzed due to clogging of RBCs at the filter, resulting in the release of several inhibitors for clinical diagnosis.

The present invention provides a novel filtration device in which particles are separated from liquid using a vertical upflow filtration chamber having a filter at the top of the chamber. In various embodiments, the device is a hemolysis-free microfluidic blood plasma separation device. By utilizing a gravity-assisted cellular sedimentation process via a vertical up-flow channel with fluid velocity transition, purified plasma without hemolysis of RBCs was successfully obtained from whole blood samples. The separated plasma volume (up to 4 µL for 30% blood hematocrit) is adequate for single-use disposable POC diagnostics, although the volume of plasma can be varied with blood hematocrit. This simple and robust hemolysis-free microfluidic blood plasma separation device could be manufactured at low-cost. Finally, our hemolysis-free device demonstrates high recovery efficiency of proteins and nucleic acids, comparable to a conventional centrifugation method, ideal for integration of downstream detection bioassays with this device.

Definitions

The term "vacuum", as used herein, refers to a state in which the interior of the device of the invention is at a pressure of less than 1 Atm. The state can be transient or stable for a selected period of time. In various embodiments, the device of the invention is stored in a device which is evacuated under a vacuum, and maintained in an evacuated state.

The term "vacuum pulse" as used herein describes a single or plurality of precisely defined changes in pressure over a period of time delivered by the pressure source. The vacuum pulse can be controlled by any electronic, chemical, thermal, negative pressure generator coupled to a power supply or by designing a specific vacuum source to deliver the desired characteristics. Furthermore, a wide variety profile of vacuum pulses, such as the square wave pulse, half-square wave pulse, sine wave pulse, half-sine wave pulse, triangular pulse, half-triangular pulse, and multi-stage pulse, can be created by commonly available controllers.

The process of "microfabrication" as described herein relates to the process used for manufacture of micrometer sized features on a variety of substrates using standard microfabrication techniques as understood widely by those skilled in this art. The process of microfabrication typically involves a combination of processes such as photolithography, wet etching, dry etching, electroplating, laser ablation, chemical deposition, plasma deposition, surface modification, injection molding, hot embossing, thermoplastic fusion bonding, low temperature bonding using adhesives and other processes commonly used for manufacture of MEMS (microelectromechanical systems) or semiconductor devices. "Microfabricated" or "microfabricated devices" as referred to herein include patterns or devices manufactured using microfabrication technology.

The term "chip", "microchip", "microfluidic device" or "microfluidic chip" as used herein means a microfluidic device generally containing a plurality of microchannels and chambers that may or may not be interconnected with each another. Typically, such microfluidic devices include one or more active or passive components such as microchannels, microvalves, micropumps, biosensors, ports, flow conduits, filters, fluidic interconnections, electrical interconnects, microelectrodes, and related control systems. More specifically the term "microfluidic device" refers to a chip that is used for detection and/or filtration of particles, e.g., cells from plasma in a whole blood sample. The microfluidic device of the invention regulates the motion of the liquids and/or particles on the chip and generally provides flow control with the aim of interaction with the physical components, such as the filter or post-filtration channel.

The term "microchannel" or "microfluidic channel", as used herein, refers to a groove or plurality of grooves created on a suitable substrate with at least one of the dimensions of the groove in the micrometer range. Microchannels can have widths, lengths, and/or depths ranging from 1 µm to 1000 µm. It should be noted that the terms "channel" and "microchannel" are used interchangeably in this description. Microchannels can be used as stand-alone units or in conjunction with other microchannels to form a network of channels with a plurality of flow paths and intersections.

The term "microfluidic" generally refers to the use of microchannels for transport of liquids and/or particles. The microfluidic system consists of a plurality of microchannels forming a network. The system optionally includes associated flow control components such as pumps, valves and filters. Microfluidic systems are ideally suited for controlling minute volumes of liquids and/or particles. Typically, microfluidic systems can be designed to handle fluid volumes ranging from the picoliter to the milliliter range.

The term "substrate" as used herein refers to the structural component used for fabrication of the micrometer sized features using microfabrication techniques. A wide variety of substrate materials are commonly used for microfabrication including, but not limited to silicon, glass, polymers, plastics, and ceramics to name a few. The substrate material may be transparent or opaque, dimensionally rigid, semi-rigid or flexible, as per the application for which they are used.

"Polymer" as used herein has the meaning normally associated with it in the art. An exemplary material is as silicone-based polymer, e.g., siloxane, e.g., polymethylsiloxane. In various embodiments, the microfluidic component of the device is fabricated from a polymer.

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof.

A "fluid sample" is any fluid from which components are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample, or a wash of an internal area of the body.

A "blood sample" as used herein can refer to a processed or unprocessed blood sample, i.e., it can be a centrifuged, filtered, extracted, or otherwise treated blood sample, including a blood sample to which one or more reagents such as, but not limited to, anticoagulants or stabilizers have been added. Blood samples include cord blood samples, bone marrow aspirates, internal blood or peripheral blood. A blood sample can be of any volume, and can be from any subject such as an animal or human. A preferred subject is a human.

A "white blood cell" is a leukocyte, or a cell of the hematopoietic lineage that is not a reticulocyte or platelet and that can be found in the blood of an animal or human. Leukocytes can include nature killer cells ("NK cells") and lymphocytes, such as B lymphocytes ("B cells") or T lymphocytes ("T cells"). Leukocytes can also include phagocytic cells, such as monocytes, macrophages, and granulocytes, including basophils, eosinophils and neutrophils. Leukocytes can also comprise mast cells.

A "red blood cell" or "RBC" is an erythrocyte. Unless designated a "nucleated red blood cell" ("nRBC") or "fetal nucleated red blood cell" or nucleated fetal red blood cell, as used herein, "red blood cell" is used to mean a non-nucleated red blood cell.

"Subject" refers to any organism, such as an animal or a human. An animal can include any animal, such as a feral animal, a companion animal such as a dog or cat, an agricultural animal such as a pig or a cow, or a pleasure animal such as a horse.

A "chamber" is a structure that is capable of containing a fluid sample, in which at least one processing step can be performed. The chamber may have various dimensions and its volume may vary between ten microliters and 0.5 liter.

A "filtration chamber" is a chamber through which or in which a fluid sample can be filtered.

A "filter" is a structure that comprises one or more pores or slots of particular dimensions (that can be within a particular range), that allows the passage of some sample components but not others from one side of the filter to the other, based on the size, shape, and/or deformability of the particles. A filter can be made of any suitable material that prevents passage of insoluble particles, such as metal, ceramics, glass, silicon, plastics, polymers, fibers (such as paper or fabric), etc.

An "automated system for separating cellular components from a blood sample" or an "automated system" is a device that comprises at least one filtration chamber, automated means for directing fluid flow through the filtration chamber, and at least one power source for providing fluid flow and, optionally, providing a signal source for the generation of forces on active chips. An automated system of the present invention can also optionally include one or more active chips, separation chambers, separation columns, or permanent magnets.

A "port" is an opening in any chamber or channel through which a fluid sample can enter or exit the chamber or channel. A port can be of any dimensions, but preferably is of a shape and size that allows a sample to be dispensed into a chamber by moving a fluid through a conduit, e.g., under vacuum, or by means of a pipette, syringe, or other means of dispensing or transporting a sample.

An "inlet" is a point of entrance for sample, solutions, buffers, or reagents into a fluidic chamber or channel. An inlet can be a port of a chamber, or can be an opening in a conduit that leads, directly or indirectly, to a chamber of a device of the invention. An inlet can itself be a chamber, e.g., the sample inlet of the instant device.

An "outlet" is the opening at which sample, sample components, or reagents exit a fluidic chamber or channel. The sample components and reagents that leave a chamber or channel can be waste, i.e., sample components that are not to be used further, or can be sample components or reagents to be recovered, such as, for example, reusable reagents or target cells to be further analyzed or manipulated. An outlet can be a port of a chamber or channel, but preferably is an opening in a conduit that, directly or indirectly, leads from a chamber or channel of the device.

"Separation" is a process in which one or more components of a sample are spatially separated from one or more other components of a sample. A separation can be performed such that one or more sample components of interest is translocated to or retained in one or more areas of a separation apparatus and at least some of the remaining components are translocated away from the area or areas where the one or more sample components of interest are translocated to and/or retained in, or in which one or more sample components is retained in one or more areas and at least some or the remaining components are removed from the area or areas. Alternatively, one or more components of a sample can be translocated to and/or retained in one or more areas and one or more sample components can be removed from the area or areas. It is also possible to cause one or more sample components to be translocated to one or more areas and one or more sample components of interest or one or more components of a sample to be translocated to one or more other areas. Separations can be achieved through, for example, filtration, or the use of physical, chemical, electrical, or magnetic forces. Nonlimiting examples of forces that can be used in separations are vacuum, gravity, mass flow, dielectrophoretic forces, traveling-wave dielectrophoretic forces, and electromagnetic forces. In exemplary embodiments, a desirable sample component, e.g., plasma, is separated from other nondesirable components of a sample, e.g., red blood cells.

In various embodiments, at least 50%, more preferably at least 70%, and further preferably, at least 80% of the desirable sample components present in the original sample are retained, and preferably at least 50%, more preferably at least 80%, even more preferably, at least 95%, and yet more preferably, at least 99%, of at least one nondesirable component of the original component is removed, from the final preparation.

The intent of defining the terms stated above is to clarify their use in this description and does not explicitly or implicitly limit the application of the present invention by modifications or variations in perception of the definitions.

The Embodiments

The Device

In an exemplary embodiment, the invention provides a microfluidic device for separating particles (e.g., red blood cells) and liquid (e.g., plasma) of a sample (e.g., whole blood sample).

Figure 2A:
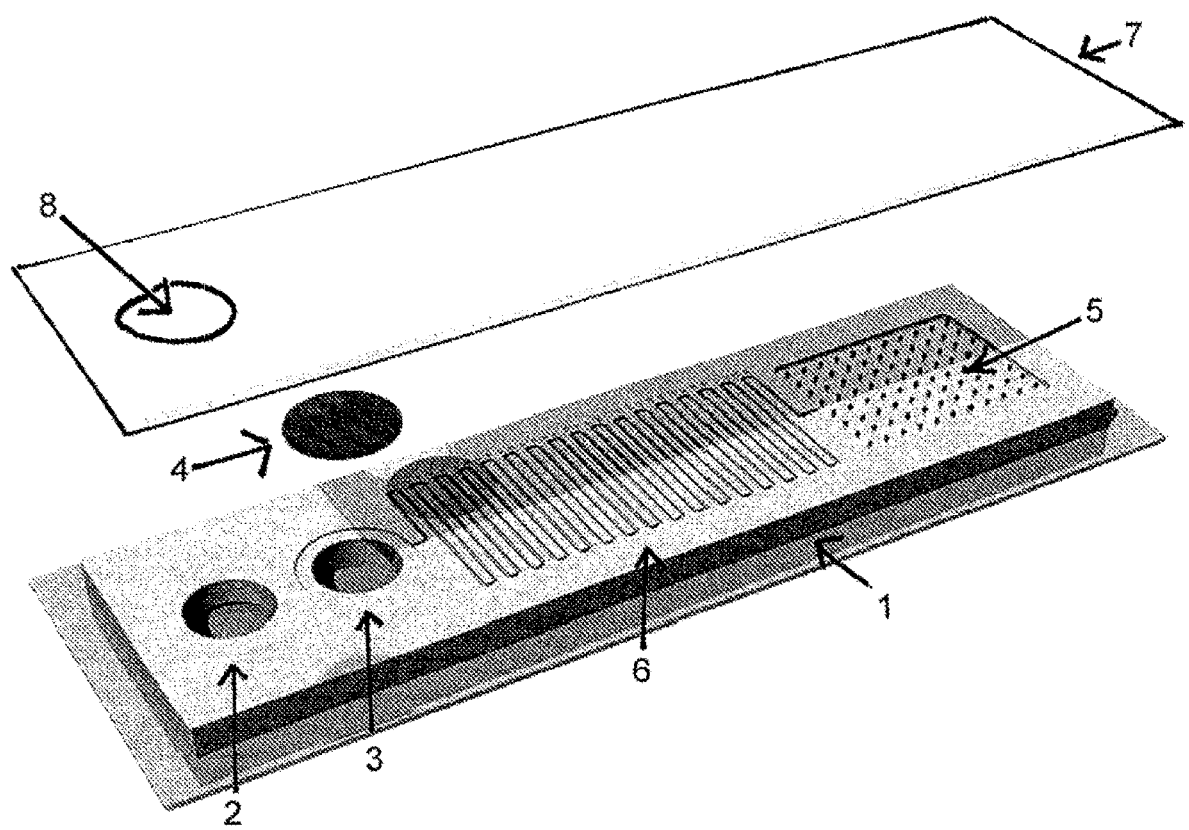
FIG. 2A. Hemolysis-free microfluidic blood plasma separation device integrated with a vertical-up flow channel. A commercially available track-etched polycarbonate membrane filter was positioned on top of the vertical up-flow channel for filtration. Inside the vertical channel, the cellular components are primarily influenced by gravitational force, leading to the prevention of cell clogging at the filter interface and continuous blood plasma separation without hemolysis.

With reference to FIG. 2A, an exemplary device includes, a microfluidic component including a sample inlet 2 configured to receive the sample and a filtration chamber 3 configured to receive a filter 4 on an upper surface of the filter chamber. The sample inlet and the filtration chamber are in fluidic communication. The filtration chamber is configured to function as a vertical upflow filtration chamber, in which the sample rises from a lower portion of the filtration chamber to an upper portion of the filtration chamber, contacts the filter and is thus filtered, removing particles, e.g., cells, which remain in the filtration chamber. A liquid component of the sample passes through the filter and can be quantified, isolated or submitted to any useful post-filtration process. In various embodiments, the device is configured to be place under vacuum such that the filtration occurs under vacuum. In an exemplary embodiment, the device is configured for separation of red blood cells and plasma in a whole blood sample.

Figure 2B:
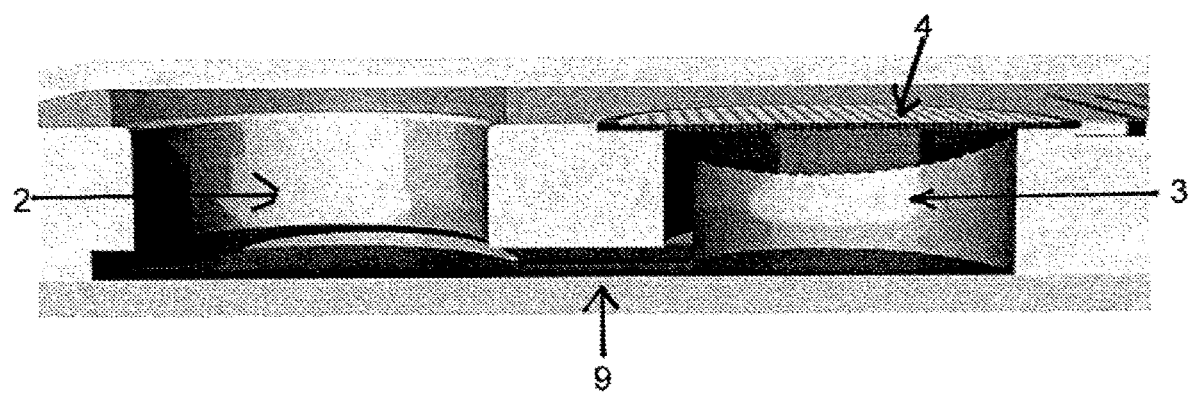
FIG. 2B. Schematic cross-sectional illustration of blood plasma separation device with filter-in-top configuration.
Figure 2C:
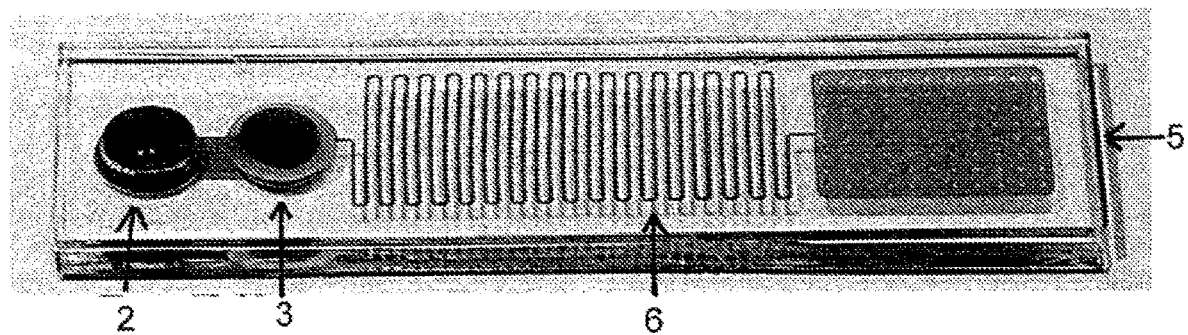
FIG. 2C. Device picture.

In various embodiments, the device of the invention is a microfluidic device for separating cellular components and plasma of a whole blood sample. With reference to FIG. 2B, the device includes: a microfluidic component comprising: a sample inlet 2 configured to receive said blood sample; a filter 4 configured for said separating; a filtration chamber 3 configured to receive said filter on an upper surface of said filter chamber; and a microfluidic channel 9 through which said sample inlet and said filtration chamber fluidically communicate.

In an exemplary device, the sample inlet and said filtration chamber fluidically communicate through a microfluidic channel disposed in a lower portion of each of the sample inlet and the filtration chamber.

A microfluidic device of the invention includes a microfluidic component configured such that the sample passes from the lower portion of the sample inlet to the lower portion of the filtration chamber through the microfluidic channel and rises to an upper portion of the filtration chamber (i.e., vertical upflow), and contacts the filter. The plasma passes through the filter, thereby separating the red blood cells from the plasma. The red blood cells drop back in to the filtration chamber via gravity sedimentation, thereby avoiding the problem of red blood cells aggregating on or adhering to the filter, diminishing the performance of the filter. FIG. 5.

Exemplary devices of the invention are set forth in the figures appended hereto.

A filtration chamber or the present invention is any chamber that can contain a fluid sample that comprises or engages at least one microfabricated filter of the present invention. A filtration chamber of the present invention can comprise one or more fluid-impermeable materials, such as but not limited to, metals, polymers, plastics, ceramics, glass, silicon, or silicon dioxide. Preferably, a filtration chamber of the present invention has a volumetric capacity of from about 0.01 milliliters to about ten liters, more preferably from about 0.2 milliliters to about two liters. In some preferred embodiments of the present invention, a filtration chamber can have a volume of from about 1 milliliter to about 80 milliliters.

In some embodiments of the present invention, a filtration chamber has at least one port that allows for the introduction of a sample into the chamber, and conduits can transport sample to and from a filtration chamber of the present invention. When fluid flow commences, sample components that flow through one or more filters can flow into one or more areas of the chamber and then out of the chamber through conduits, and, preferably but optionally, from the conduits into a vessel, such as a collection chamber. The filtration chamber can also optionally have one or more additional ports for the additions of one or more reagents, solutions, or buffers.

Figure 2D:
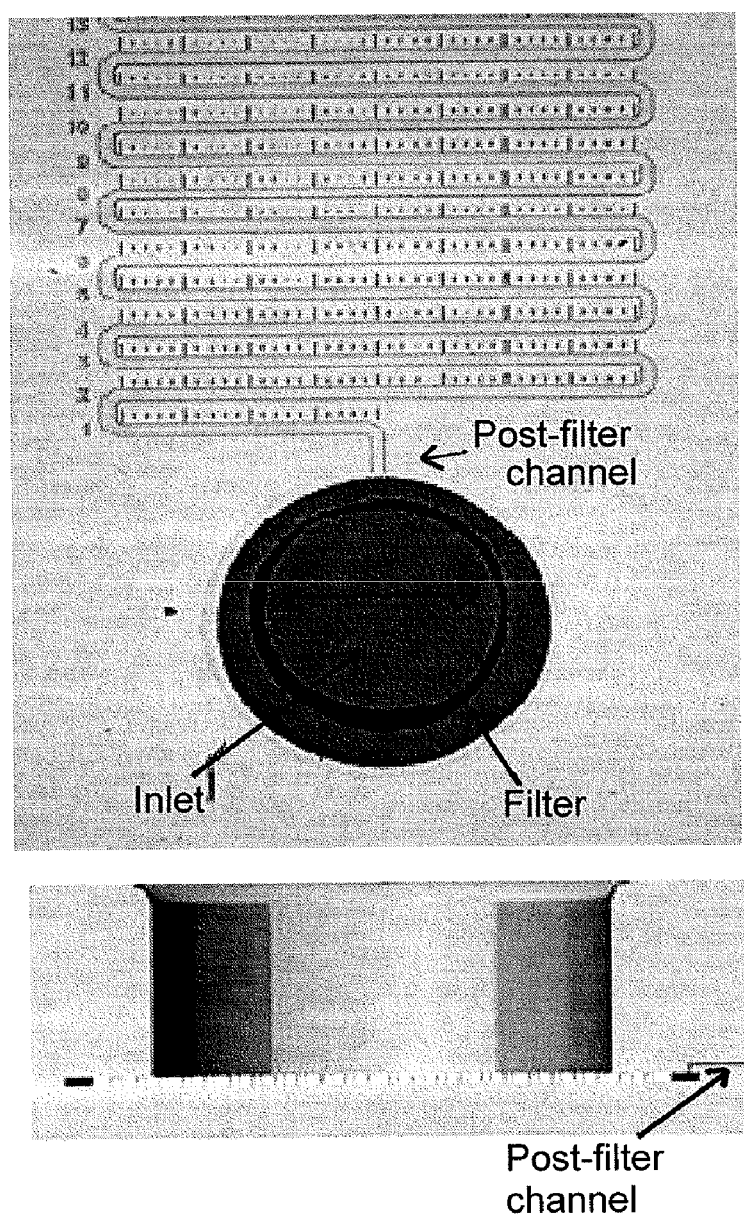
FIG. 2D. Device picture and cross-sectional illustration of blood plasma device with filter-in-bottom configuration.
Figure 2E:
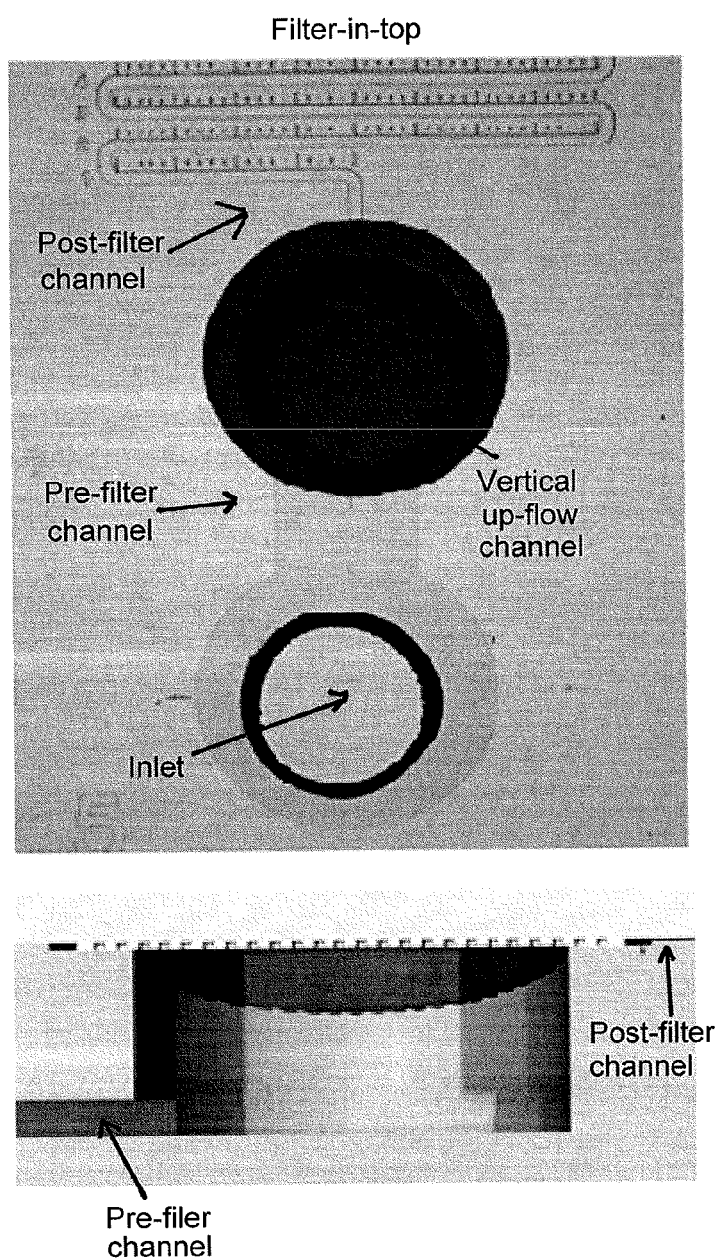
FIG. 2E. Device picture and cross-sectional illustration of blood plasma device with filter-in-top configuration.

In an exemplary embodiment, the filtration chamber fluidically communicates with one or more inlet for providing sample to the filtration chamber. In various embodiments, the filtration chamber fluidically communicates with one or more outlets through which a component of the sample is removed following filtration. In an exemplary embodiment, the one or more outlet is disposed above the filter located at the top of the filtration chamber and the sample component filtered through the filter flows through the outlet to another component of the device. FIG. 2E, FIG. 3B.

In an exemplary embodiment, the sample inlet and the filtration chamber are fluidically connected by a microfluidic channel 9, connecting with a lower portion of each of the sample inlet 2 and the filtration chamber 3. In operation, when the device is under vacuum, the sample is transferred from the sample inlet through the microfluidic channel and in to the filtration chamber.

The filtration chamber may include one or more surface contours to affect the flow of a sample, a solution such as wash or elution solution or both. For example contours may deflect, disperse or direct a sample to assist in the spreading of the sample along the chip. Alternatively, contours may deflect, disperse or direct a wash solution such that the wash solution washes the chamber or chip with greater efficiency. Such surface contours may be in any appropriate configuration. The contours may include surfaces that project generally toward the chip or may project generally away from the chip. They may generally encircle the chip. Contours may include but are not limited to projections, recessed portions, slots, deflection structures such as ball-like portions, bubbles (formed from e.g. air, detergent, or polymers), and the like. Contours such as two or more slots may be configured generally parallel to one another yet generally angled when viewing the chamber upright to direct flow in a generally spiraled path.

Figure 2F:
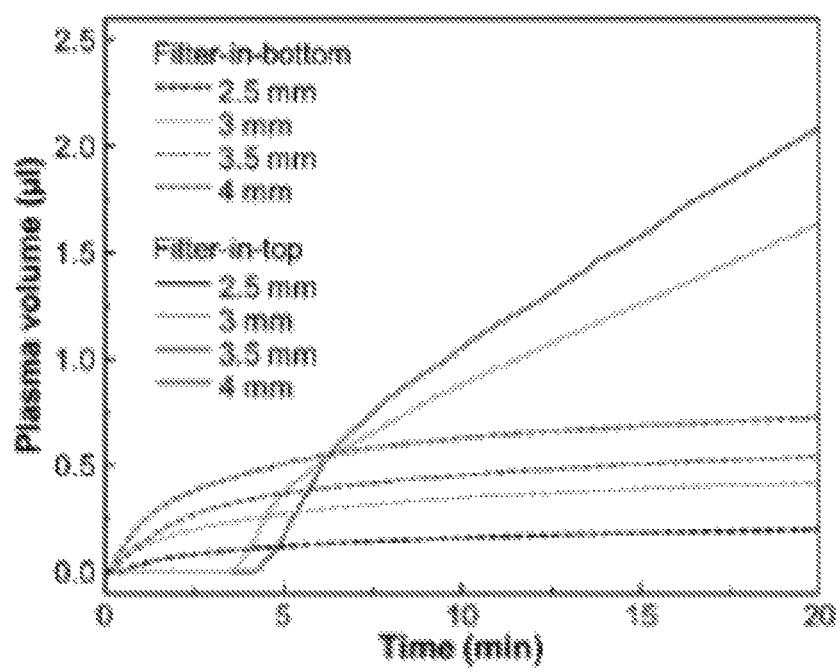
FIG. 2F. Measured plasma volume with different channel diameters as a function of time. Separated plasma volume measured 20 min after blood drop with changes of FIG. 2G inlet and vertical up-flow channel diameter and FIG. 2H blood hematocrit levels.
Figure 2G:
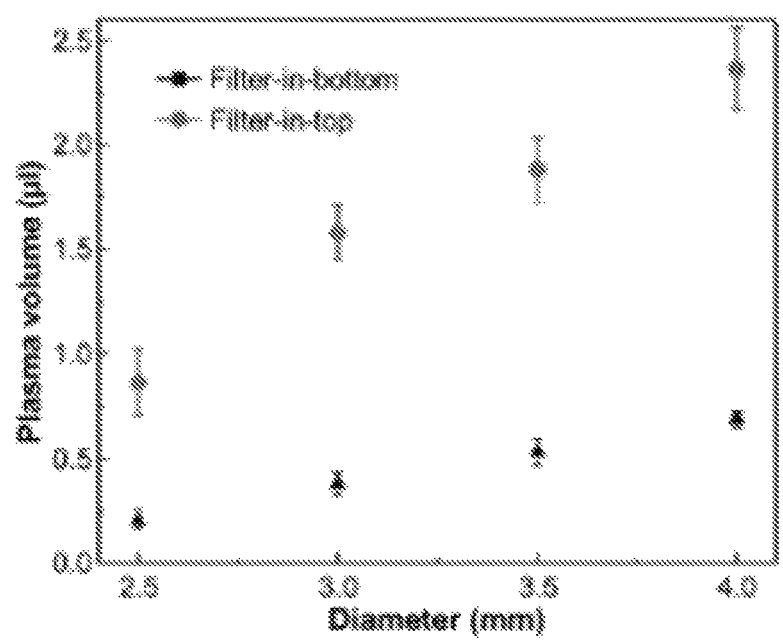
FIG. 2G. Plot of plasma volume vs. channel diameter as a function of time. Separated plasma volume measured 20 min after blood drop with changes of FIG. 2H inlet and vertical up-flow channel diameter.
Figure 2H:
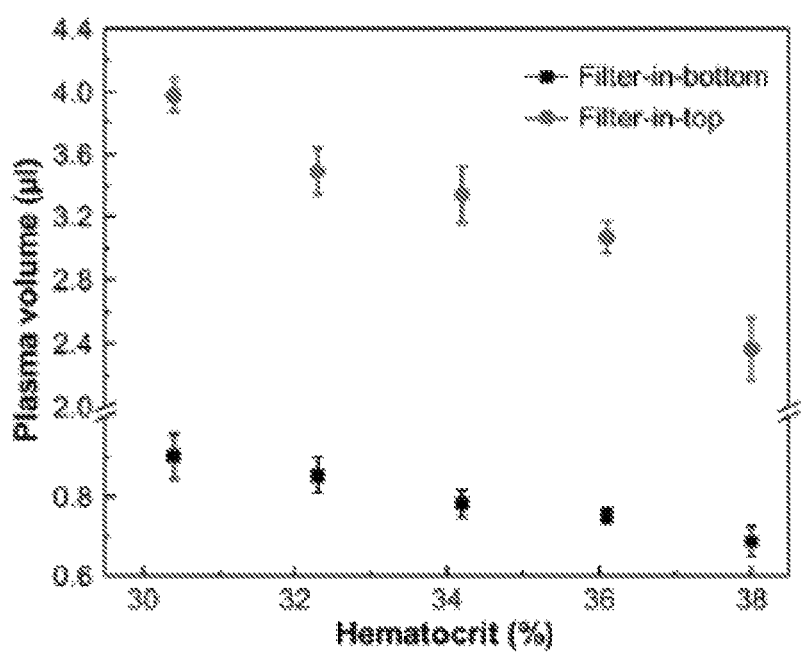
FIG. 2H. Plot of plasma volume vs. hematocrit.
Figure 2I:
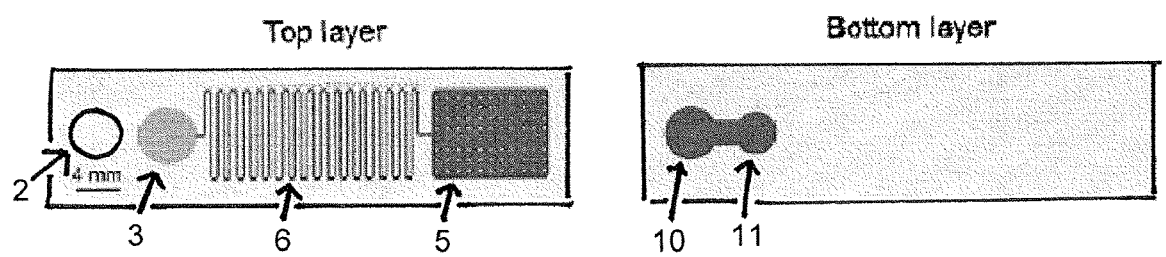
FIG. 2I. Design of upper and lower PDMS subunits of microfluidic component.
Figure 2J:
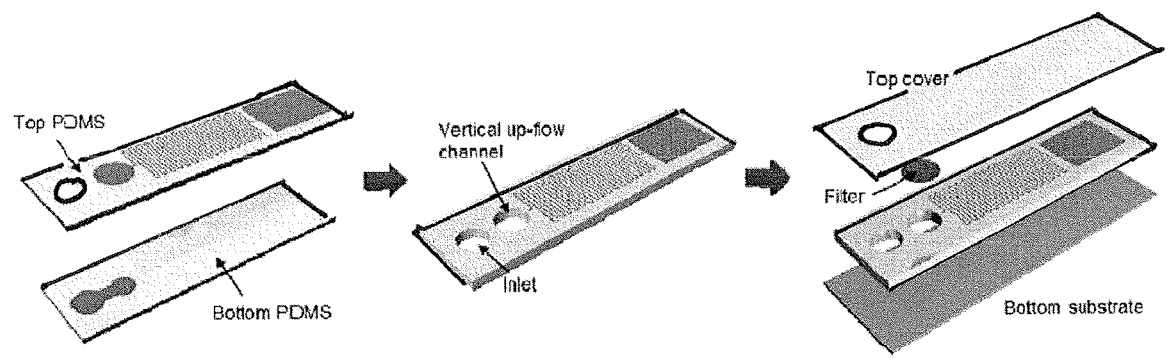
FIG. 2J. Fabrication process of filter-in-top microfluidic blood plasma separation device. First, top and bottom PDMS layers were bonded together after $O_2$ plasma treatment. The inlet and vertical up-flow channel were created with a Harris Uni-Core™ punch. The PDMS layer was attached to bottom plastic substrate, and a membrane filter (5 mm) was placed on top of the vertical up-flow channel. Finally, the top cover plastic was bonded to the top PDMS layer.

With reference to FIG. 2I and FIG. 2J, in various embodiments, the microfluidic device includes a microfluidic component fabricated from an upper subunit (top layer) and a lower subunit (bottom layer). The upper subunit and the lower subunit are mated subunits and are bonded together. In an exemplary device, the upper subunit includes a first port for the sample inlet 2 and a first port for the filtration chamber 3, each communicating with an upper surface of the upper subunit.

In various embodiments, the device of the invention includes a microfluidic component in which the sample inlet includes a second port and the filtration chamber includes a second port, wherein each of the second ports is in a lower surface of said upper subunit. Prior to assembly, the first and second ports of the sample inlet and the filtration surface penetrate the upper and lower surface, respectively of the upper subunit, creating passages through this subunit. In this configuration, before assembly with the lower subunit, the sample inlet and filtration chamber are not in fluid communication.

In various embodiments, the upper subunit is mated with and bonded to a lower subunit. An exemplar lower subunit includes a first depression 10 and a second depression 11, each formed in an upper surface thereof. When the upper subunit and the lower subunit are mated, the first depression fluidically communicates with the lower portion of the sample inlet. The second depression fluidically communicates with the lower portion of the filtration chamber. The first depression and the second depression fluidically communicate with each other, thereby bringing in to fluidic communication the sample inlet and the filtration chamber of the assembled microfluidic component.

In various embodiments, the microfluidic component of the device is bonded to a substrate 1 (FIG. 2A). Exemplary substrates are fabricated of rigid materials, e.g., metals, plastics, glasses. Furthermore, in an exemplary embodiment, an upper surface of the microfluidic component of the device is bonded to a cover 7 (FIG. 2A). The cover includes a through hole port 8 aligned with the sample inlet port when it is bonded to the upper surface of the upper subunit of the microfluidic component. Exemplary materials for the cover include clear plastics and glasses, such that the fluid in the microfluidic device below is observable by eye or optical instrumentation.

Exemplary devices of the invention include a microfluidic component in which the upper subunit further comprises a post-filtration void, which is a member selected from a post-filtration microfluidic channel 6, a collection chamber and a combination thereof. The void optionally includes an outlet providing outside access to the collection chamber for removal of the sample, or addition of analytical reagents or other substances.

In an exemplary embodiment, the filtration chamber is fabricated to include a narrow circular protrusion or lip of a diameter slightly smaller than that of the filtration chamber below the upper surface of the upper subunit upon which the filter rests.

A microfluidic device of the present invention can have means for sensing the volume of a fluid, such as, but not limited to, the volume of a fluid sample, including a fluid sample supernatant. In an exemplary embodiment, the fluid volume sensing means is a ruled microfluidic channel. An exemplary channel includes numeric or other readable marking adjacent the microfluidic channel, which marking allows determination of the volume of fluid in the device 6 (FIG. 2A), and FIG. 3B.

In various embodiments, the means for sensing the volume of a fluid relies on optical sensing, such as detection of transmittance, absorption, reflectance, or fluorescence, and can comprise a light source, such as a light bulb, laser, or LED, and a sensing structure such as CCDs or photomultipliers appropriately aligned with the light source or sources. Thus the volume sensing means can comprise a light transmission-light sensing system that does not rely on contacting the sample to detect volume. Wavelengths for particular sensing applications can be readily determined, for example, for turbidity (600 nm), or the absorbance of particular sample components. A light source that is part of a light transmission-light sensing system can transmit light in the non-visible range, such as the ultraviolet or infrared range.

For example, the fraction of a sample that comprises red blood cells can be detected using light in the range of 700 to 900 nanometers, more preferably between 750 and 850 nanometers.

In various embodiments, the component of the sample passing through the filter passes to a volume sensing component of the device, where its volume is quantified or otherwise evaluated.

In an exemplary embodiment, the collection chamber includes one or more outlet facilitating the removal of the sample component that passed through the filter and was collected in the collection chamber.

In various embodiments, the outlet for the filtration chamber, collection chamber and/or volume sensing means is fluidically coupled to, or configured to be fluidically coupled to one or more devices downstream of the device of the invention. The downstream devices can include any device of use in analytic method or separation. Thus, exemplary downstream devices include separation devices (e.g., chromatography columns, electrophoretic devices), detection/monitoring devices (e.g., UV/Vis, mass spectrometer), reactors (e.g., reaction with a detectable agent, an antibody, an enzyme).

In various embodiments, the inlet of the filtration chamber fluidically communicates, or is configured to fluidically communicate with one or more device upstream from the filtration chamber. As will be appreciated by those of skill in the art, such devices can be configured to deliver samples to the filtration chamber and include conventional, art-recognized devices for accomplishing this aim. Such upstream devices can also be of use to pre-filter or otherwise purify or concentrate the sample before it is introduced in to the filtration chamber.

In an exemplary embodiment, the device includes one or more inlets and/or outlets communicating with fluid handling devices, e.g., pumps, syringes and the like. Exemplary locations for such inlets and or outlets include, without limitation, the sample inlet, the outlet of the filtration chamber, and a port accessing the collection chamber for removal of sample or addition of test reagents or other species.

In an exemplary embodiment, the device is packaged in or otherwise maintained in an evacuated environment. The device, upon removal from the evacuated environment is ready for use, e.g., without the need for applying additional vacuum during its use. In an exemplary embodiment, the device includes a suction member, or a vacuum reservoir 5 (FIG. 2A), which modulates the pressure in the microfluidic component of the device during its use, e.g., maintains the pressure in the device below about 1 Atm for at least a portion of the separation process, thereby providing motive force moving the fluid and particles through the device. The vacuum reservoir communicates fluidically with at least one other feature of the microfluidic component of the device, e.g., the collection chamber, filter chamber, sample inlet or a combination thereof.

The Methods

The present invention provides methods of separating cells of a fluid sample using filtration through a filter using a device or system of the present invention. The method includes: dispensing a sample into a filtration chamber that comprises or engages at least one filter that comprises at least one filter at the top of the chamber; providing upwards vertical fluid flow of the sample through the filtration chamber, such that components of the fluid sample flow through or are retained by the filters based on the size, shape, or deformability of the components; and collecting the portion of the sample which passed through the filter and/or the cells from said filtration chamber. In some embodiments, filtration can separate soluble and small components of a sample from at least a portion of the cells that are in the sample, in order to concentrate the retained cells to facilitate further separation and analysis. In some aspects, filtration can remove undesirable components from a sample, such as, but not limited to, undesirable cells. Where filtration reduces the volume of a sample by at least 50% or removes greater than 50% of the cellular components of a sample, filtration can be considered a debulking step. The present invention contemplates the use of filtration for debulking as well as other functions in the processing of a fluid sample, such as, for example, concentration of sample components or separation of sample components (including, for example, removal of undesirable sample components and retention of desirable sample components).

Sample

A sample can be any fluid sample, such as an environmental sample, including air samples, water samples, food samples, and biological samples, including suspensions, extracts, or leachates of environmental or biological samples. Biological samples can be blood, a bone marrow sample, an effusion of any type, ascities fluid, pelvic wash fluid, or pleural fluid, spinal fluid, lymph, serum, mucus, sputum, saliva, urine, semen, occular fluid, extracts of nasal, throat or genital swabs, cell suspension from digested tissue, or extracts of fecal material. Biological samples can also be samples of organs or tissues, including tumors, such as fine needle aspirates or samples from perfusions of organs or tissues. Biological samples can also be samples of cell cultures, including both primary cultures and cell lines. The volume of a sample can be very small, such as in the microliter range, and may even require dilution, or a sample can be very large, such as up to about two liters for ascites fluid.

The present invention is exemplified by reference to blood samples, however, those of skill in the art will understand that the devices, systems and methods of the invention are not limited to such separations. A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

In an exemplary embodiment, the sample is a whole blood sample. Hemolysis, involving the rupture of red blood cells (RBCs) and release of their contents into blood plasma, is a major issue of concern in clinical fields. Hemolysis in vitro can occur as a result of errors in clinical trials; in vivo, hemolysis can be caused by a variety of medical conditions. Blood plasma separation is often the first step in blood-based clinical diagnostic procedures. However, inhibitors released from RBCs due to hemolysis during plasma separation can lead to problems in diagnostic tests such as low sensitivity, selectivity and inaccurate results. In particular, a general lack of simple and reliable blood plasma separation methods has been a major obstacle for microfluidic-based point-of-care (POC) diagnostic devices.

In various embodiments, the invention provides a hemolysis-free microfluidic blood plasma separation platform and method of using this platform. A membrane filter was positioned on top of a vertical up-flow channel (filter-in-top configuration) to reduce clogging of RBCs by gravity-assisted cells sedimentation. According to this method, separated plasma volume was increased about at least 2-, 3, or 4-fold (e.g., 2.4 µL plasma after 20 min with 38% hematocrit human whole blood). In an exemplary embodiment, hemoglobin concentration in separated plasma was decreased approximately 70%, 80% 90% or 95% due to the prevention of RBCs hemolysis, when compared to conventional filter-in-bottom configuration blood plasma separation platforms. In various embodiments, on-chip plasma isolated by a method of the invention contained ~90% of protein and ~100% of nucleic acids found in off-chip centrifuged plasma, confirming comparable target molecule recovery efficiency. FIG. 2F, FIG. 2G, FIG. 2H, FIG. 6B, FIG. 7A, FIG. 7B, FIG. 7C, and FIG. 7D.

In an exemplary embodiment, there is provided a method of separating plasma from cellular components in a whole blood sample using a device of the invention. The method includes: (a) adding the whole blood sample to said sample inlet through said sample inlet port; (b) transferring the whole blood sample from the sample inlet to the filtration chamber through the microfluidic channel communicating with the sample inlet and the filtration chamber, such that the sample flows vertically from a lower portion of the filtration chamber to an upper portion of the filtration chamber, contacting said filter; (c) transferring a liquid component of the whole blood sample through the filter and retaining within the filtration chamber a solid component of the whole blood sample, e.g., red blood cells. The separating is performed under conditions selected such that the solid component of said whole blood sample does not adhere to the filter and drops in to the filtration chamber. In various embodiments, the device and method are configured such that the reduced pressure inside the device and the geometry of the structures within the microfluidic component of the device facilitate gravity sedimentation of the red blood cells and decrease or essentially eliminate clogging of the filter by red blood cells adhering thereto.

Exemplary methods of the invention make use of devices of the invention that are evacuated, such that pressure within the device is less than about 1 Atm. The evacuation can be achieved by means of a vacuum apparatus communicating with the interior of the device, e.g., through a vacuum port. Alternatively, the device can be evacuated and maintained in an evacuated state until use. An exemplary method of the invention uses such an evacuated device, without further application of a source of vacuum during the filtration process.

Method of Manufacture

Traditionally, microfluidic devices have been constructed in a planar fashion using techniques that are borrowed from the silicon fabrication industry. Representative systems are described, for example, in some early work by Manz et al. (*Trends in Anal. Chem.* (1990) 10(5): 144-149; *Advances in Chromatography* (1993) 33: 1-66). In these publications, microfluidic devices are constructed by using photolithography to define channels on silicon or glass substrates and etching techniques to remove material from the substrate to form the channels. A cover plate is bonded to the top of the device to provide closure. Miniature pumps and valves can also be constructed to be integral to such devices. Alternatively, separate or off-line evacuation or pumping mechanisms are of use.

More recently, a number of methods have been developed that allow microfluidic devices to be constructed from plastic, silicone or other polymeric materials. In one such method, a negative mold is first constructed, and plastic or silicone is then poured into or over the mold. The mold can be constructed using a silicon wafer (see, e.g., Duffy et al., *Analytical Chemistry* (1998) 70: 4974-4984; McCormick et. al., *Analytical Chemistry* (1997) 69: 2626-2630), or by building a traditional injection molding cavity for plastic devices. Some molding facilities have developed techniques to construct extremely small molds. Components constructed using a LIGA technique have been developed at the Karolsruhe Nuclear Research center in Germany (see, e.g., Schomburg et al., *Journal of Micromechanical Microengineering* (1994) 4: 186-191), and commercialized by MicroParts (Dortmund, Germany). Jenoptik (Jena, Germany) also uses LIGA and a hot-embossing technique. Imprinting methods in PMMA have also been demonstrated (see, Martynova et al., Analytical Chemistry (1997) 69: 4783-4789).

Various conventional surface machining or surface micromachining techniques such as those known in the semiconductor industry may be used to fashion channels, vias, and/or chambers in these materials. For example, techniques including wet or dry etching and laser ablation may be used. Using such techniques, channels may be made into one or more surfaces of a first substrate. A second set of channels may be etched or created in a second substrate. The two substrates are then adhered or otherwise fastened together in such as way that the channels surfaces are facing one another and certain regions may be overlapped to promote mixing.

The microfabricated devices of the present invention can be made by using microfabrication or micromachining techniques on substrate materials, including, but not limited to, silicon, silicon dioxide, ceramics, glass, polymers such as polydimethylsiloxane, polyimide, polyamide, etc. Various fabrication methods, as known to those skilled in the art of microlithography and microfabrication (See, for example, Rai-Choudhury P. (Editor), Handbook of Microlithography, Micromachining and Microfabrication, Volume 2: Micromachining and microfabrication. SPIE Optical Engineering Press, Bellingham, Wash., USA (1997)), may be used. In many cases, standard microfabrication and micromachining methods and protocols may be involved. One example of suitable fabrication methods is photolithography involving single or multiple photomasks. The protocols in the microfabrication may include many basic steps, for example, photolithographic mask generation, deposition of photoresist, deposition of "sacrificial" material layers, photoresist patterning with masks and developers, or "sacrificial" material layer patterning. Pores can be made by etching into the substrate under certain masking process so that the regions that have been masked are not etched off and the regions that have not been mask-protected are etched off. The etching method can be dry-etching such as deep RIE (reactive ion etching), laser ablation, or can be wet etching involving the use of wet chemicals.

Still further embodiments may be fabricated from various materials using well-known techniques such as embossing, stamping, molding, and soft lithography. Additionally, in yet another embodiment, the layers are not discrete, but instead a layer describes a substantially planar section through such a device. Such a microfluidic device can be constructed using photopolymerization techniques such as those described in Cumpston, et al. (1999) *Nature* 398:51-54.

In an exemplary embodiment, microfluidic devices according to the present invention are constructed using standard soft lithography replica molding techniques to define compartments and channels for transporting fluids.

In an exemplary embodiment, the process uses negative photoresist and a silicon wafer. An exemplary photoresist layer is substantially planar and defines one or more microstructures such as channels.

Notably, lithography-based fabrication methods enable very rapid fabrication of robust microfluidic devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

A wide variety of materials may be used to fabricate microfluidic devices of the invention, including polymeric, metallic, and/or composite materials, to name a few. In an exemplary embodiment, microfluidic devices according to the present invention are fabricated from materials such as glass, silicon, silicon nitride, quartz, or similar materials. In exemplary embodiments, however, polymeric materials are used due to their inertness and each of manufacture.

When the device includes more than one layer, in an exemplary embodiment, two or more such layers mate with each other and are fastened in to an appropriate alignment. In an exemplary embodiment, an adhesive is used to fix the more than one layer in the desired alignment. Other techniques may be used to attach one or more of the various layers of microfluidic devices useful with the present invention, as would be recognized by one of ordinary skill in attaching materials. For example, attachment techniques including thermal, chemical, or light-activated bonding; mechanical attachment (including the use of clamps or screws to apply pressure to the layers); or other equivalent coupling methods may be used.

The following examples are offered to illustrate various embodiments of the invention and should not be construed as limiting.

EXAMPLES

Example 1

Experimental

For the filter-in-top configuration, the device was fabricated by placing a 1.8 mm thick poly(dimethylsiloxane) (PDMS) layer between two 1 mm thick plastic sheets (PSS-3000, Piedmont Plastics) (FIG. 2I and FIG. 2J). The PDMS layer consisted of two separate PDMS layers, bonded together after $O_2$ plasma treatment. The top and bottom microfluidic channels face the top and bottom plastic sheets, respectively. Top channels contain a ruler to measure the volume of separated plasma. The two channels were connected by a vertical up-flow channel created with a variable size of Harris Uni-Core™ punch. A Nuclepore™ track-etched polycarbonate membrane filter with 0.4 μm pores purchased from Whatman was used for blood plasma separation. The membrane filter was placed between the top PDMS layer and plastic sheet. For the filter-in-bottom device, a 1.8 mm thick single PDMS layer with ruler was bonded with a bottom plastic sheet. The filter was placed below the inlet of the device.

For fluid actuation, degas-driven fluid flow in PDMS microfluidic devices (Dimov, et al., *Lab Chip*, 2011, 11:845-850; Randall, et al., *Proc. Natl. Acad. Sci. U.S.A.*, 2005, 102:10813-10818) was used, since self-powered actuation without an external power source is highly desirable for POC diagnostics. The device was activated by maintaining it in a vacuum desiccator with low pressure (<0.3 atm) for 2 hrs. After removing the device from the low pressure environment, the whole blood sample was loaded into the inlets of the device within 2 min of removing the device from the low pressure environment. Acid-citrate-dextrose (ACD) anticoagulant treated human whole blood was purchased from Bioreclamation Inc., with the initial hematocrit content of blood at 38% and diluted with phosphate buffered saline (PBS) buffer to obtain a lower hematocrit level.

To demonstrate the protein and nucleic acid recovery efficiency after plasma separation, conventional bench-top centrifugation, sedimentation and on-chip blood plasma separation from whole blood were employed. Sedimentation was performed by leaving vials to settle cellular components in a 4° C. refrigerator for 2 hrs. Centrifugation was performed at 1000×g for 5 minutes. A bicinchoninc acid (BCA) protein assay (Thermo Scientific) was used to determine protein concentration in separated blood plasma. The BCA protein assay measures the reduction of $Cu^+$ from $Cu^{2+}$ in alkaline solutions containing proteins using BCA for colorimetric detection. Whole blood was diluted with PBS in a 1:10 ratio before plasma separation. All plasma samples were incubated for 30 min at 37° C. before their absorbance at 562 nm was measured. Total RNA was extracted from a NSCLC cell line, HCC827, purchased from ATCC, through a conventional TRIZOL method according to the manufacturer's protocol. The extracted total RNA was subsequently reverse-transcribed into the template DNA via an RT-PCR protocol, the first stranded cDNA synthesis using Moloney Murine Leukemia Virus Reverse Transcriptase (M-MLV RT). Then total template DNA ranging from 0.032 to 32 ng/ml was spiked into the blood samples. For target DNA amplification, we used the TaqMan® probe gene assay via the quantitative polymerase chain reaction (qPCR) to monitor their amplification threshold.

Results and Discussion

Design for Hemolysis-free Blood Plasma Separation

Figure 1B:
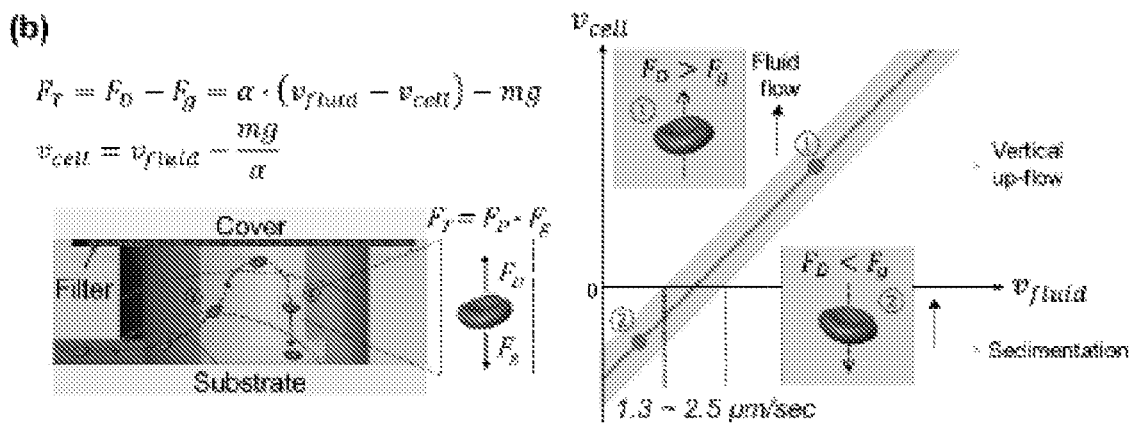
FIG. 1B. To prevent hemolysis, the filter was placed on top of a vertical up-flow channel (filter-in-top design) for gravity-assisted cellular sedimentation in the vertical channel. Figure shows simplified cell movement in the vertical up-flow channel, where RBCs are exposed to fluidic drag force (FD) and gravitational force (Fg). The calculated transition fluid velocity, vfluid, from vertical up-flow to sedimentation, is calculated to be in the range of 1.3 to 2.5 µm/sec. Red dot line:schematic streamline of whole blood sample; Blue dot line:schematic streamline of RBCs.

FIG. 1A shows a schematic illustration of blood plasma separation with a membrane filter. For the filter-in-bottom configuration, where the filter is positioned below the microfluidic channel inlet, the clogging of RBCs at the filter interface can cause hemolysis due to high shear stress, resulting in the release of unwanted inhibitors for clinical diagnosis. To prevent hemolysis, we propose placing the filter on top of a vertical up-flow channel (filter-in-top design) as shown in FIG. 1B. In this configuration, the gravitational force ($F_g$), which is opposite to fluidic drag force ($F_D$), can attract the RBCs toward the bottom of device in the vertical up-flow channel, decreasing clogging at the filter interface. With this filter configuration, we can separate blood plasma without hemolysis of RBCs.

An analytical model was applied for optimal design of the filter-in-top configuration, simplified as a vertical motion of single RBCs. Along the fluidic flow, RBCs are exposed to both fluidic drag forces and gravitational forces; the drag force, at a low Reynolds number, is linearly related to the difference between cell velocity and fluidic velocity; the gravitational force downward is proportional to cell mass (Phillips, et al., *Physical Review Lett.*, 2012, 109:118105).

Figure 1C:
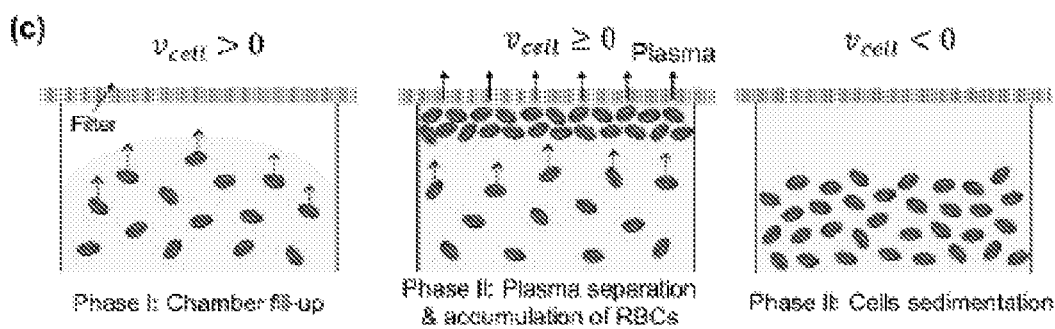
FIG. 1C. Schematics of cell movement transition from vertical up-flow to sedimentation during blood plasma separation.

The drag coefficient (α in the figure) was calculated for a 3-dimensional RBCs (FIG. 5A-FIG. 5C). If $v_{fluid}$ is large enough for the drag force to be stronger than the gravitational force, cell movement is upward ($v_{fluid}$>0, i.e. region ①); if not, RBCs will instead precipitate downward ($v_{fluid}$<0, i.e. region ②). The model calculations reveal a transition of $v_{fluid}$ in the range of 1.3 to 2.5 µm/sec, assuming that cell mass and size varies within 10 percentage points of the standard (Phillips, et al., Physical Review Lett., 2012, 109:118105) and that cell orientation varies with the drag coefficient, α. Our filter-in-top device requires a $v_{fluid}$ below the transition velocity in order to avoid RBCs clogging at the filter; yet, $v_{fluid}$ is practically designed to be transient from a high (region ①) to a low velocity (region ②) across by a pressure drop at the filter, as shown in FIG. 1C, since a higher initial velocity will ultimately increase the separated plasma volume by reducing the time to fill up vertical channel (Phase I). If the blood reaches the filter, the pressure will drop due to the filter resistance, resulting in the decrease of fluid velocity. The accumulation of RBCs layers below the filter, acting as a filter cake, will further decrease the fluid velocity due to the additional pressure drop (Phase II), and finally allow the RBCs to precipitate by gravitational force (Phase III).

Characterization of Blood Plasma Separation

FIG. 2A shows a picture and schematic illustration of the microfluidic blood plasma separation device integrated with a vertical up-flow channel for gravity-assisted cellular sedimentation, to prevent clogging of the filter as well as hemolysis of RBCs. We have used commercially available track-etched polycarbonate membrane filters with a 0.4 µm pore size for blood plasma separation and degas-driven autonomous fluid actuation for POC diagnostics. The filter was placed on top of the vertical up-flow channel and in this configuration, blood samples flow from the bottom channel to the top channel through the vertical up-flow channel. The gravitational force on the cellular components in the solution prevents clogging of the filter interface with cells, allowing for continuous blood plasma separation without hemolysis. FIG. 2D shows the pictures and schematic cross-sectional images of fabricated filter-in-bottom (left) vs. filter-in-top (right) blood plasma separation devices. The diameter, d, indicates the diameter of the inlet in the filter-in-bottom device, and the vertical up-flow channel in the filter-in-top device, respectively. FIG. 2F shows the separated plasma volume as a function of time with different channel diameters. For the filter-in-bottom device, the plasma was observed within 30 sec after blood drop, while separated plasma volume was rapidly saturated due to clogging of RBCs at the filter interface. For the filter-in-top device, it is noteworthy that the plasma volume continuously increased without saturation. This is attributed to the gravity-assisted cell sedimentation. Although the volume of plasma increased in the filter-in-bottom devices with an increase in inlet diameter, we could obtain larger volumes of plasma in the filter-in-top devices, as shown in FIG. 2G. The plasma recovery yield of a filter-in-top device with a 4 mm channel diameter is approximately 20% after 20 min, but increases further with time, as the blood plasma can continuously undergo separation without saturation due to filter clogging. The plasma recovery yield can be further increased by optimizing the channel dimensions and characteristics of the degas-driven fluid actuation. In addition, large volumes of plasma can be easily achieved by increasing the size of the filter and vertical up-flow channel, and by potentially integrating multiple filters and channels for multiplexed downstream biomarker detection. FIG. 2H shows the changes in separated plasma volume with different blood hematocrit levels. With a decrease in hematocrit level, the plasma volume was increased and no blood cells were observed in separated plasma (not shown here).

Table 1 summarizes the average fluid velocity of the filter-in-top device with different vertical channel diameters (FIG. 7A-FIG. 7D). For phase I, the fluid velocity was decreased with an increase of channel diameter, because it requires more time for blood to fill up the larger vertical up-flow channel with fixed degas-driven flow. It is noteworthy that the fluid velocities for all channel diameters were found to be faster than transition $v_{fluid}$ (1.3~2.5 µm/sec). However, the average fluid velocities (calculated from separated plasma volume) for phase III were found to be much slower than the transition $v_{fluid}$, leading to gravity-assisted RBCs sedimentation and subsequent hemolysis-free blood plasma separation.

TABLE 1

Average fluid velocity of filter-in-top blood plasma separation device with different channel diameters.

| | Average fluid velocity (µm/sec) | | |
|---|---|---|---|
| Channel diameter (mm) | Phase I (whole blood) | Phase II (plasma) | Phase III (plasma) |
| 2.5 | 10 | 0.27 | 0.14 |
| 3 | 8.6 | 0.45 | 0.18 |
| 3.5 | 7.2 | 0.36 | 0.17 |
| 4 | 4.4 | 0.27 | 0.19 |

Blood Plasma Separation without Hemolysis

Figure 3A:
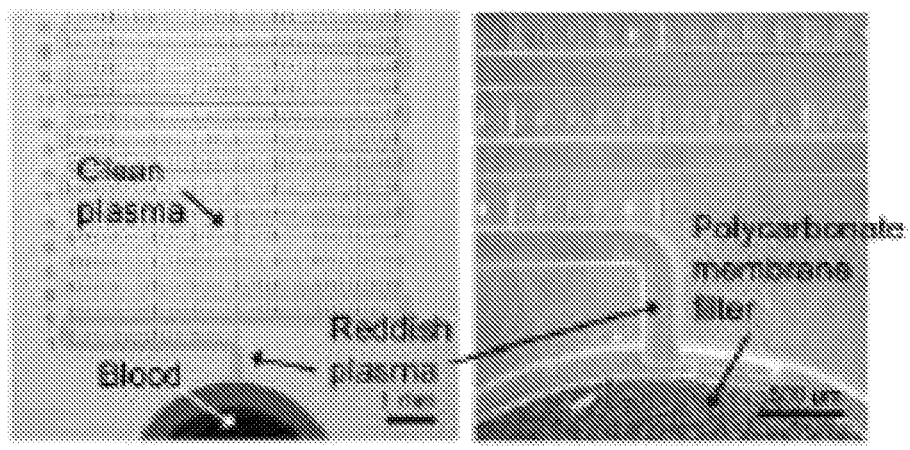
FIG. 3. Hemolysis of RBCs and plasma purity. Optical microscope images of separated blood plasma with FIG. 3A filter-in-bottom and FIG. 3B filter-in-top microfluidic blood separation devices.
FIG. 3C. Optical microscope images and absorbance spectrum of collected plasmas with different blood plasma separation methods. Hemolysis of RBCs was significantly reduced with the filter-in-top configuration.
Figure 3B:
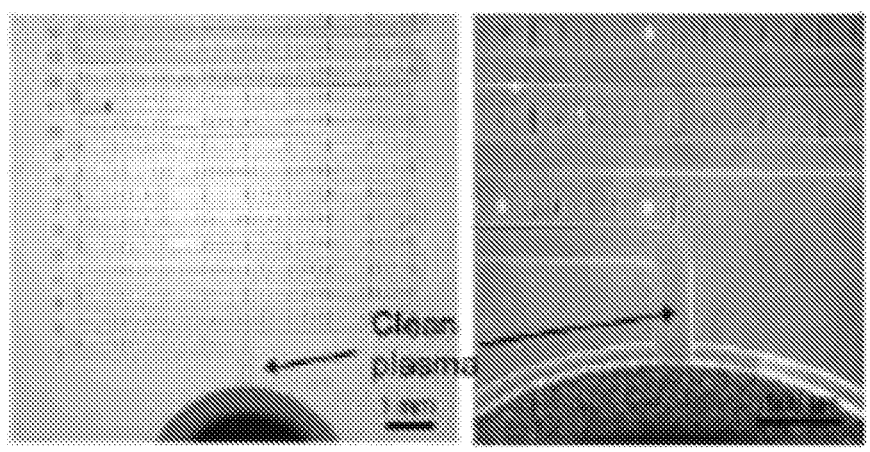
Figure 3C:
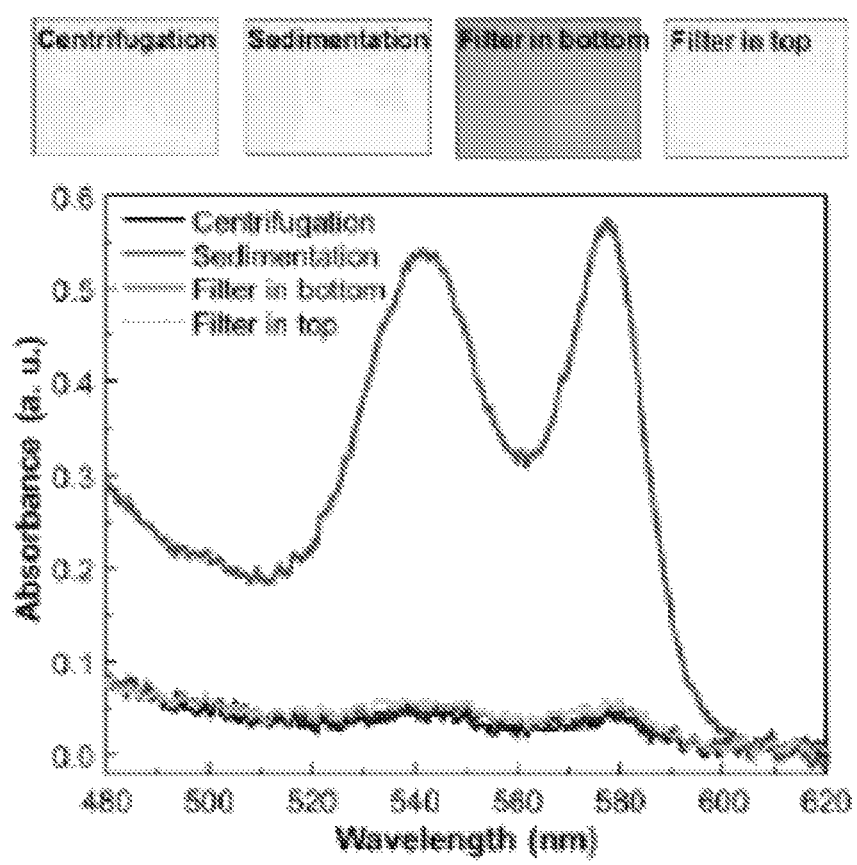

FIG. 3A and FIG. 3B show optical microscope images of the filter-in-bottom and filter-in-top plasma separation devices after plasma separation, confirming that no cellular components leakage such as RBCs and WBCs were observed. For the filter-in-bottom device, the separated plasma was clean at first but became reddish due to the hemolysis of RBCs. However, for the filter-in-top device, hemolysis was not observed during the duration of observation. We measured the absorbance spectra of the plasma obtained via different blood plasma separation methods to compare the hemoglobin concentration in separated plasma. Absorbance peaks at 541 and 576 nm are attributed to free hemoglobin in the plasma (Al-Soud, et al., J. Clin. Microbiol., 2001, 39(2):485-493). The plasma separated using the filter-in-top device shows similar levels of hemoglobin as conventional centrifugation and sedimentation methods, showing comparable result to previous work (Zhang, et al., Anal. Chem., 2012, 84:3780-3786). The weak absorbance peaks for the plasma samples separated with centrifugation, sedimentation and filter-in-top device could be attributed to the release of hemoglobin from the RBCs with storage period after blood collection (for our experiments, at least 3 days from collection at company to usage at laboratory) as previously reported (S. O. Sowemimo-Coker, Transfus Med Rev, 2002, 16:46-60). However, in the case of the filter-in-bottom device, the hemoglobin concentration was significantly increased, up to 14-fold, due to the hemolysis of RBCs as shown in FIG. 3A.

Separated Plasma Shows High Target Molecules Recovery Efficiency

Figure 4A:
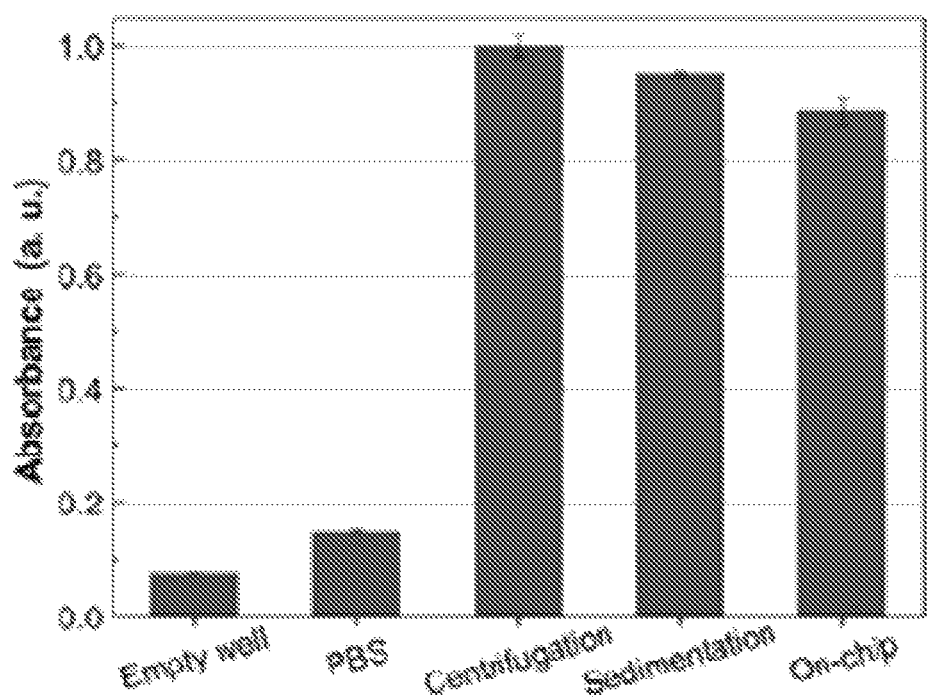
FIG. 4A. BCA colorimetric protein assay results showing plasma protein recovery with different blood plasma separation methods. Absorbance was measured at 562 nm wavelength.
Figure 4B:
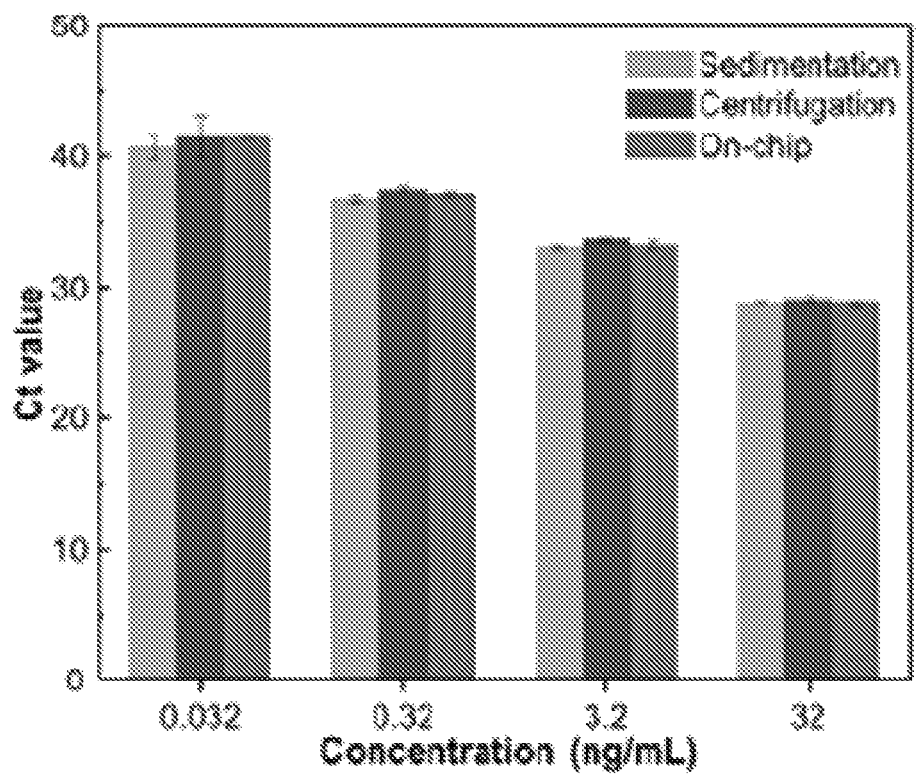
FIG. 4B. qPCR results with different blood plasma separation methods. Whole blood was spiked with various concentrations of cMET nucleic acids.
Figure 6A:
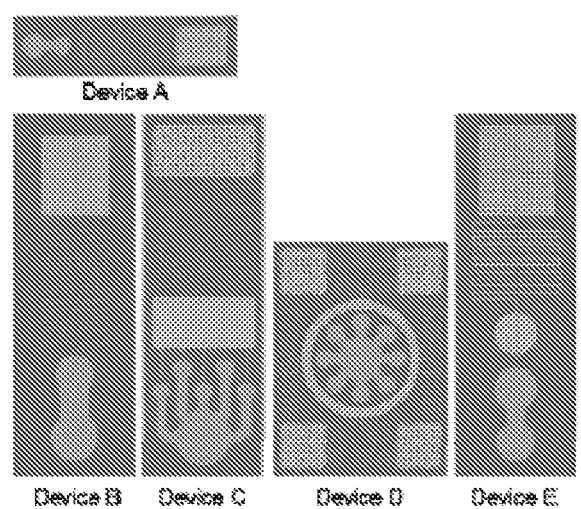
FIG. 6A Several microfluidic blood plasma separation devices with large filter (device B, E) and multiple filters (device C, D) for increased plasma volume.
Figure 6B:
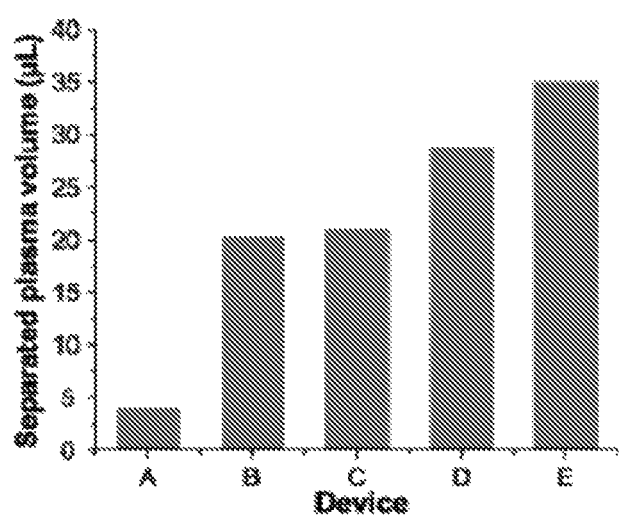
FIG. 6B. Separated plasma volume measured 20 min after blood drop with different device design.
Figure 7A:
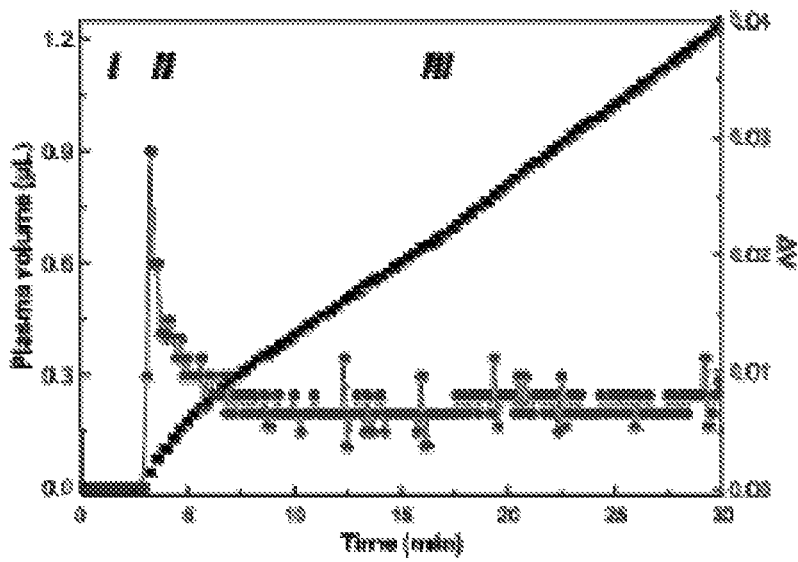
FIG. 7. Measured plasma volume (left axis) and changes of plasma volume ($v_2-v_1$) per unit time (right axis) of 2.5 mm (FIG. 7A); 3.0 mm (FIG. 7B); 3.5 mm (FIG. 7C); 4.0 mm (FIG. 7D) in filter-in-top blood plasma separation device.
Figure 7B:
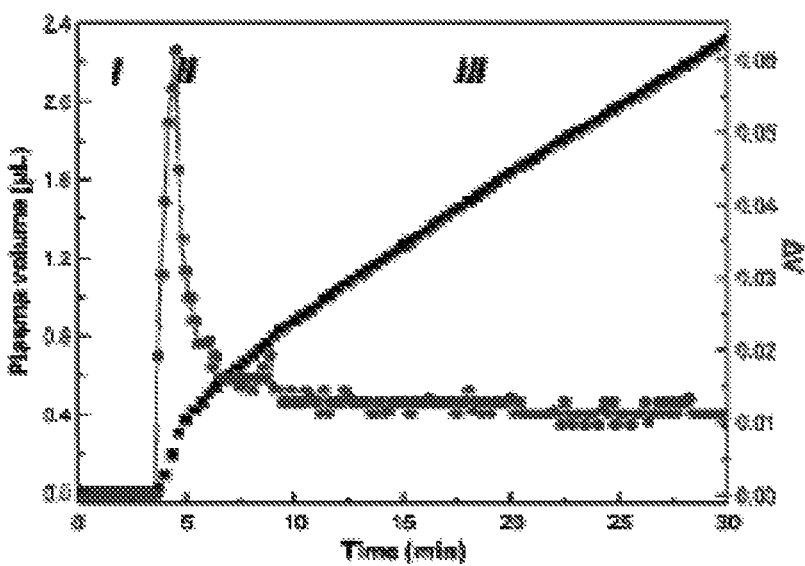
Figure 7C:
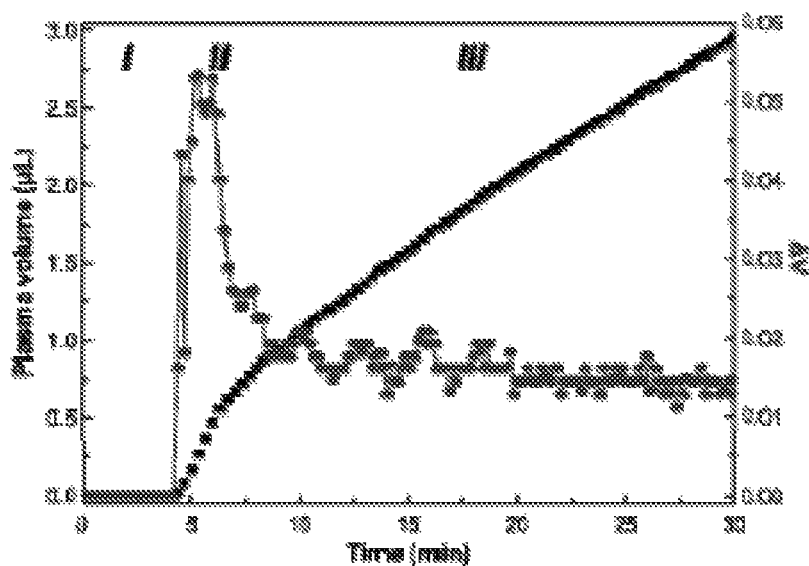
Figure 7D:
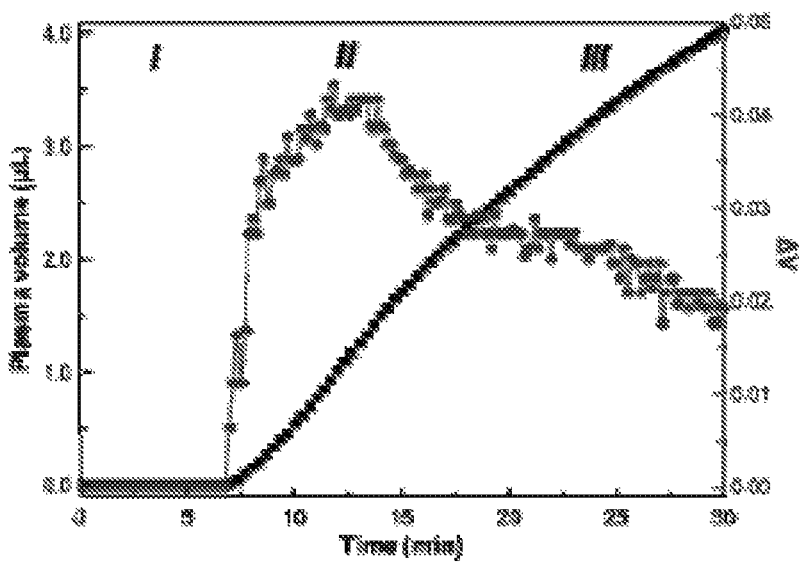

In order to check compatibility with downstream diagnostic assays after blood plasma separation, we tested downstream protein and nucleic acid recovery with BCA protein assay and qPCR amplification on a target total cDNA. FIG. 4A shows the BCA protein assay results, showing total protein recovery from different blood plasma separation methods. The plasma separated using centrifugation, sedimentation and the filter-in-top device were collected and total protein amount was analyzed via BCA protein assay. With reference to traditional centrifugation methods, the on-chip plasma shows 89% protein recovery yield. For the nucleic acids recovery, blood samples were prepared by spiking the target total cDNA (cMET, lung cancer biomarker (Cheng, et al., Chest, 2005, 128:1453-1460) with clinically relevant ranges (Sozzi, et al., J. Clin. Oncol. 2003, 21:3902-3908) (from 0.032 ng/ml to 32 ng/ml). As shown in the FIG. 4B, by comparing their qPCR threshold values, we found that there were negligible differences in nucleic acid recovery between the three methods, which supports the validity of our developed on-chip blood plasma separation method. These results demonstrate that the microfluidic blood plasma separation device with a filter-in-top configuration has potential for use in clinical testing with downstream detection assays, with minimal loss of target protein and nucleic acids.

Hemolysis-free blood plasma separation is based on gravity-assisted cells sedimentation, governed by force balance between the fluidic drag force ($F_D$) and gravitational force ($F_g$). However, significant shape change of RBCs by some pathological condition (such as sickle cell disease or malaria) could affect the transition fluid velocity for sedimentation, although we considered 10% variation in the cell mass and size of normal RBCs for the calculation of transition fluid velocity. Another potential limitation would be the decrease of separated plasma volume with high hematocrit levels in case of newborns, dehydration and diseases such as erythrocytosis, congenital heart disease. Therefore, the device design would be further optimized to separate blood plasma without hemolysis for medical diagnosis regardless of the morphology of RBCs and blood hematocrit level. Lastly, the timely loading of whole blood sample after removing the device from the low pressure environment is important to have enough degas-driven fluid flow for blood plasma separation in PDMS microfluidic devices.

Fabrication of Microfluidic Blood Plasma Separation Device

The microfluidic channels were fabricated using standard soft lithography replica molding techniques. Briefly, a mold for the top layer was created through a double-layer process using negative photoresist and a silicon wafer. The 5 μm-thick first layer (blue circle in FIG. 2J) for embedment of membrane filter was fabricated with SU8-3005 (Microchem U.S.A.). The diameters of the first layer and membrane filter were 5.5 and 5 mm, respectively. To prevent leakage of RBCs, the thickness of first layer was designed to be lower than that of membrane filter (~8 μm). The 80 μm-thick second layer, which includes ruler markings to measure the separated plasma volume, was fabricated with SU8-3035 (Microchem U.S.A.). The width of the second layer channel was 200 μm. For the bottom layer, a mold was created through a 100 μm-thick single-layer process using negative photoresist, SU8-2100 (Microchem U.S.A.) on a silicon wafer. PDMS (Sylgard 184, Dow Corning) was prepared with a 10:1 mass ratio (base to cross-linker); degassed in a vacuum chamber for 30 min; then poured on the SU8 mold to a thickness of ~0.9 mm for each layer; then cured in an oven at 60° C. for at least 2 h. The PDMS was then carefully peeled off the mold. FIG. 2J shows the fabrication process of filter-in-top device.

Calculation of Drag Coefficient

The drag coefficient of single red blood cells (RBCs) was calculated by fluidic simulation with a 3-dimensional RBCs model as shown in FIG. 5A-FIG. 5C. The sectional shape of the model was based on Ref 26 (Shardt, et al., International Journal of Multiphase Flow, 2012, 47:25-36) and revolved along the z-axis. A uniform flow was applied to x-, y-, and z-direction and each drag force was calculated. The average value of three drag forces normalized by flow velocity was taken as the drag coefficient, since drag force is linearly proportional to the drag coefficient in low Reynolds number.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

1. Kersaudy-Kerhoas, et al., Lab Chip, 2013, 13:3323-3346.
2. Lippi, et al., Critical Reviews in Clinical Laboratory Sciences, 2011, 48(3):143-153.
3. L. J. Kricka, Clinical Chemistry, 2000, 46(8):1037-1038.
4. Al-Soud, et al., J. Clin. Microbiol., 2001, 39(2):485-493.
5. Kirschner, et al., PLoS ONE, 2011, 6(9):e24145.
6. Kabanova, et al., Int. J. Med. Sci. 2009, 6(4):156-159.
7. Chin, et al., Nat. Medicine, 2011, 17:1015-1019.
8. Song, et al., Nat. Communication, 2012, 3:1283.
9. Yager, et al., Nature, 2006, 442:412-418.
10. Chin, et al., Lab Chip, 2007, 7:41-57.
11. Chin, et al., Lab Chip, 2012, 12:2118-2134.
12. Davis, et al., Proc. Natl. Acad. Sci. U.S.A., 2006, 103:14779-14784.
13. Zhang, et al., Anal. Chem., 2012, 84:3780-3786.
14. Dimov, et al., Lab Chip, 2011, 11:845-850.
15. Lenshof, et al., Anal. Chem., 2009, 81:6030-6037.
16. Mach, et al., Biotechnol. Bioeng., 2010, 107:302-311.
17. Cho, et al., Lab Chip, 2007, 7:565-573.
18. Lee, et al., Lab Chip, 2013, 13:3261-3267.
19. Ji, et al., Biomed Microdevices, 2008, 10:251-257.
20. Thorslund, et al., Biomed Microdevices, 2006, 8:73-79.
21. Randall, et al., Proc. Natl. Acad. Sci. U.S.A., 2005, 102:10813-10818.
22. Phillips, et al., Physical Review Lett., 2012, 109:118105.
23. S. O. Sowemimo-Coker, Transfus Med Rev, 2002, 16:46-60.
24. Cheng, et al., Chest, 2005, 128:1453-1460.
25. Sozzi, et al., J. Clin. Oncol. 2003, 21:3902-3908.
26. Shardt, et al., International Journal of Multiphase Flow, 2012, 47:25-36.

What is claimed is:

1. A microfluidic device for separating cellular components from plasma of a whole blood sample, said device comprising:
 a microfluidic component comprising:
  a sample inlet configured to receive said blood sample;
  a filter configured for said separating;
  a filtration chamber configured to retain said filter on an upper surface of said filtration chamber; and
  a microfluidic channel through which said sample inlet and said filtration chamber fluidically communicate
 wherein the microfluidic channel is disposed in a lower portion of each of said sample inlet and said filtration chamber.

2. The microfluidic device according to claim 1, wherein said filtration chamber is configured as a vertical upflow filtration chamber.

3. The microfluidic device according to claim 2, wherein said microfluidic component is configured such that said sample passes from said lower portion of said sample inlet to said lower portion of said filtration chamber through said microfluidic channel and rises to an upper portion of said filtration chamber, contacts said filter, said plasma transversing said filter, thereby separating said cellular components from said plasma.

4. The microfluidic device according to claim 1, wherein said microfluidic component is fabricated from an upper subunit and a lower subunit, wherein said upper subunit and said lower subunit are mated subunits and bonded together.

5. The microfluidic device according to claim 4, wherein said lower subunit comprises a first depression and a second depression, each formed in an upper surface thereof, such that when said upper subunit and said lower subunit are mated, said first depression fluidically communicates with said lower portion of said sample inlet and said second depression fluidically communicates with said lower portion of said filtration chamber, and wherein said first depression and said second depression fluidically communicate with each other via the microfluidic channel, thereby bringing in to fluidic communication said sample inlet and said filtration chamber.

6. The microfluidic device according to claim 4, wherein said upper subunit comprises a first port for said sample inlet and a first port for said filtration chamber, each communicating with an upper surface of said upper subunit.

7. The microfluidic device according to claim 6, wherein said sample inlet comprises a second port and said filtration chamber comprises a second port, wherein each said second port is in a lower surface of said upper subunit.

8. The microfluidic device according to claim 6, wherein said upper subunit further comprises a post-filtration void, which is a member selected from a post-filtration microfluidic channel and a collection chamber and a combination thereof, wherein said void is in fluidic communication with an outlet for said filtration chamber.

9. The microfluidic device according to claim 8, wherein said post-filtration void is a post-filtration microfluidic channel, and wherein said post-filtration microfluidic channel is configured as a serpentine channel.

10. The microfluidic channel according to claim 8, wherein said post-filtration void is a post-filtration microfluidic channel, and wherein said upper surface of said upper subunit further comprises markings corresponding to volume adjacent said post-filtration microfluidic channel.

11. The microfluidic device according to claim 8, wherein said post-filtration void is a collection chamber, and wherein said collection chamber further comprises a port fluidically communicating therewith through which a filtered component of said sample can be withdrawn or one or more substances can be injected, thereby contacting said filtered component of said sample.

12. The microfluidic device according to claim 6, wherein said upper or lower subunit further comprises a suction chamber configured to maintain an ambient atmosphere of less than about 1 Atm.

13. The microfluidic device according to claim 12, wherein said suction chamber is in direct or indirect fluidic communication with said filtration chamber.

14. The microfluidic device according to claim 1, wherein a lower surface of said microfluidic component is bonded to a substrate.

15. The microfluidic device according to claim 1, wherein an upper surface of said microfluidic component is bonded to a cover, wherein said cover comprises a through hole port aligned with said sample inlet port.

16. The microfluidic device according to claim 1, wherein said microfluidic component is fabricated from a polymer.

17. The microfluidic device according to claim 16, wherein said polymer is polydimethylsiloxane.

18. The microfluidic device according to claim 1, wherein said cellular components are red blood cells, white blood cells, or platelets.

19. A method of separating plasma from red blood cells in a whole blood sample using the device according to claim 1, said method comprising:
   (a) adding said whole blood sample to said sample inlet through a sample inlet port;
   (b) transferring said whole blood sample from said sample inlet to said filtration chamber through said microfluidic channel communicating with said sample inlet and said filtration chamber, such that said sample flows vertically from the lower portion of said filtration chamber to an upper portion of said filtration chamber and contacts said filter;
   (c) transferring a liquid component of said whole blood sample through said filter and retaining within said filtration chamber a solid component of said whole blood sample,
   wherein said separating, is performed under conditions selected such that said solid component of said whole blood sample does not adhere to said filter and drops in to said filtration chamber.

20. The method according to claim 19, wherein said device is evacuated such that pressure within said device is less than about 1 Atm.

21. The method according to claim 19, wherein said separating is completed to a selected level without application of external vacuum to said device during said separating.

* * * * *